United States Patent [19]

Yanagisawa et al.

[11] Patent Number: 4,778,790
[45] Date of Patent: Oct. 18, 1988

[54] PERHYDROTHIAZEPINE AND PERHYDROAZEPINE DERIVATIVES AND THEIR THERAPEUTIC USE

[75] Inventors: Hiroaki Yanagisawa; Sadao Ishihara; Akiko Ando; Hiroyuki Koike; Yasuteru Iijima, all of Hiromachi, Japan

[73] Assignee: Sankyo Company Limited, Tokyo, Japan

[21] Appl. No.: 35,489

[22] Filed: Apr. 3, 1987

[30] Foreign Application Priority Data

Apr. 4, 1986 [JP] Japan .................................. 61-77904
Aug. 5, 1986 [JP] Japan ................................. 61-183576

[51] Int. Cl.⁴ .................. C61K 31/55; A61K 31/395; C07D 281/06; C07D 225/02
[52] U.S. Cl. ...................................... 514/211; 514/63; 514/212; 540/487; 540/488; 540/524; 540/527
[58] Field of Search ............... 540/488, 524, 527, 487; 514/211, 212, 63

[56] References Cited

U.S. PATENT DOCUMENTS

| 4,587,050 | 5/1986 | Harris et al. | 540/463 |
| 4,629,787 | 12/1986 | Harris et al. | 540/527 |
| 4,666,901 | 5/1987 | Parsons | 540/527 |
| 4,680,392 | 7/1987 | Harris et al. | 540/527 |
| 4,699,905 | 10/1987 | Yanagisawa et al. | 514/211 |
| 4,734,410 | 3/1988 | Yanagisawa et al. | 514/212 |

FOREIGN PATENT DOCUMENTS

| 46291 | 2/1981 | European Pat. Off. | 540/527 |
| 68173 | 1/1983 | European Pat. Off. | 514/211 |
| 120728 | 10/1984 | European Pat. Off. | 540/488 |
| 161801 | 11/1985 | European Pat. Off. | 514/211 |

OTHER PUBLICATIONS

Chemical Abstracts vol. 106, Item 32870g (1987) abstracting South African Patent ZA 80 04,755 (Feb. 26, 1986).
Chemical Abstracts vol. 106, Item 78243h (1987) abstracting Thorsett "Actual Chim. Ther.", (1986), vol. 13, pp. 257-268.
Thorsett et al, Peptides Structure and Function, Am. Peptide Symposium (8th: 1983) Univ. of Arizona, pp. 556-588.

*Primary Examiner*—Robert T. Bond
*Attorney, Agent, or Firm*—Frishauf, Holtz, Goodman & Woodward

[57] ABSTRACT

Compounds of formula (I):

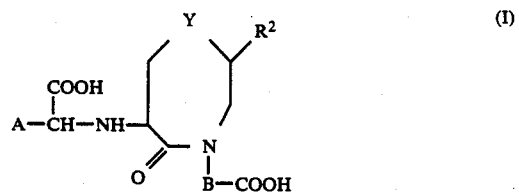

(wherein A is an alkylene group substituted by an optionally substituted amino or heterocyclic group and optionally interrupted by an oxygen or sulfur atom, $R^2$ is various organic groups, B is $C_1$–$C_2$ alkylene and Y is sulfur or methylene) and pharmaceutically acceptable salts and esters thereof are valuable hypotensive agents which may be prepared by a condensation reaction of the corresponding compound having an amino group in place of the group A—CH(COOH)—NH—.

44 Claims, No Drawings

PERHYDROTHIAZEPINE AND PERHYDROAZEPINE DERIVATIVES AND THEIR THERAPEUTIC USE

BACKGROUND TO THE INVENTION

The present invention relates to a series of perhydrothiazepine and perhydroazepine derivatives which have the valuable ability to lower blood pressure and hence which are of potential use in the treatment of humans and other animals suffering from elevated blood pressure.

There is considerable evidence that reduction of elevated blood pressure reduces the risks of morbidity and mortality. Elevated blood pressure (hypertension) can be caused by a variety of factors and a large number of drugs is available for the treatment of hypertension, the drug of choice being dictated in large measure by the cause of the hypertension, as well as the degree of hypertension and the acceptance of the treatment by the patient. One of the known causes of hypertension is the presence in blood plasma of the polypeptide known as angiotension II, and a reduction in the blood plasma levels of angiotensin II has been shown to reduce hypertension. The first step in the production of angiotensin II in the mammalian body is the conversion of a blood protein, by the enzyme renin, to a polypeptide known as "angiotensin I". This angiotensin I is then converted by angiotensin converting enzyme (hereinafter referred to, as is conventional, as "ACE") to angiotensin II. The enzyme ACE has another metabolic function, namely it participates in the metabolism of bradykinin, a natural vasodilator, converting it to an inactive metabolite.

Hence, the enzyme ACE is capable of raising blood pressure by two routes: one is the production of angiotensin II, which itself directly raises blood pressure; the second is the inactivation of bradykinin which, through its vasodilatory activity, tends to reduce blood pressure. There has, therefore, been considerable interest in recent years in the development of compounds having the ability to inhibit the activity of ACE.

For example, certain perhydro-1,4-thiazepin-5-one derivatives are disclosed in U.S. patent application Ser. No. 721 303, filed 9 Apr. 1985 which issued as U.S. Pat. No. 4,699,905; these thiazepine derivatives differ from those of the present invention principally in the nature of the substituent at the 6-position. Also, certain perhydroazepin-2-one derivatives are disclosed in U.S. patent application Ser. No. 917 041, filed 9 Oct. 1986; these azepine derivatives also differ from those of the present invention principally in the nature of the substituent at the 3-position.

Other close prior art relevant to the azepine derivatives of the present invention is European Patent Publication No. 46 291, which discloses a series of perhydroazepin-2-one (or caprolactam) derivatives having substituents at the 1- and 3-positions and optionally also having a substituent at the 7-position. The compounds of European Patent Publication No. 46 291, however, unlike the compounds of the present invention, are unsubstituted at the 6-position. Surprisingly, we have found that the compounds of the present invention have several advantages over the prior art compounds of European Patent Publication No. 46 291, including a higher ACE inhibitory activity and a longer duration of this activity in vivo.

There is also a mention of certain 1,4-thiazepine derivatives similar to those of the present invention in European Patent Publication No. 156 455, but the 1,4-thiazepine derivatives disclosed therein differ from those of the present invention in that they have a benzene ring fused to the thiazepine ring at the 2- and 3-positions The compounds of the present invention have the advantages over the prior art compounds of higher activity and a longer duration of activity, in general than the prior art compounds, even, in some cases greater than that of U.S. patent application Ser. No. 721 303. Moreover, they are believed to be potentially more useful for oral administration, which, is well known, is normally the preferred route of administration for this type of drug.

BRIEF SUMMARY OF INVENTION

It is, therefore, an object of the present invention to provide a series of perhydrothiazepine and perhydroazepine derivatives which have exceptional ACE inhibitory activity.

It is a further object of the invention to provide pharmaceutical compositions containing such a perhydrothiazepine or perhydroazepine derivative as an ACE inhibitor agent.

It is a still further object of the present invention to provide methods for the treatment or prophylaxis of angiotensin-induced hypertension in animals (including human beings) by the administration thereto of such a perhydrothiazepine or perhydroazepine derivative.

The compounds of the present invention are those compounds of formula (I):

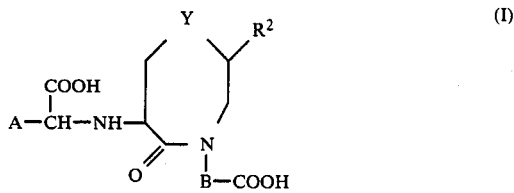

wherein:
A represents a group of formula (i):

or a group of formula (ii):

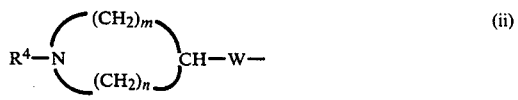

in which:
$R^4$ and $R^5$ are independently selected from the group consisting of hydrogen atoms, $C_1$-$C_6$ alkyl groups and amino-protecting groups;

Z represents a $C_1$-$C_8$ alkylene group;

W represents a $C_1$-$C_6$ alkylene group or a group of formula $—(CH_2)_k—X—(CH_2)_l—$, wherein X represents an oxygen or sulfur atom, k represents the cypher 0 or an integer from 1 to 5 and l represents an integer from 1 to 5; and m and n are the same or different and each represents an integer from 1 to 6;

R$^2$ represents a C$_1$–C$_{10}$ alkyl group, a C$_3$–C$_8$ cycloalkyl group, a C$_6$–C$_{10}$ aryl group or a heterocyclic group having 5 ring atoms, of which from 1 to 3 are hetero-atoms selected from the group consisting of nitrogen, oxygen and sulfur atoms, said aryl and heterocyclic groups being unsubstituted or having at least one substituent selected from the group consisting of substituents (a), defined below:

B represents a C$_1$–C$_2$ alkylene group;

Y represents a sulfur atom or a methylene (CH$_2$) group; and substituents (a):

C$_1$–C$_6$ alkyl groups, aralkyl groups wherein the alkyl part is C$_1$–C$_6$ alkyl and the aryl part is C$_6$–C$_{10}$ carbocyclic aryl which has from 0 to 3 substituents selected from the group consisting of substituents (a), hydroxy groups, C$_1$–C$_6$ alkoxy groups, C$_6$–C$_{10}$ carbocyclic aryl groups having from 0 to 3 substituents selected fron the group consisting of substituents (a), aralkyloxy groups where the alkyl part is C$_1$–C$_6$ alkyl and the aryl part is C$_6$–C$_{10}$ carbocyclic aryl which has from 0 to 3 substituents selected from the group consisting of substituents (a), C$_6$–C$_{10}$ aryloxy groups, halogen atoms, nitro groups, cyano groups, carboxy groups, alkoxycarbonyl groups having a total of from 2 to 7 carbon atoms, amino groups, C$_1$–C$_6$ alkylamino groups, dialkylamino groups wherein each alkyl part is C$_1$–C$_6$ alkyl, aliphatic or carbocyclic aromatic carboxylic acylamino groups, carbamoyl groups, alkylcarbamoyl groups where the alkyl part is C$_1$–C$_6$ alkyl, dialkylcarbamoyl groups where each alkyl part is C$_1$–C$_6$ alkyl, mercapto groups, C$_1$–C$_6$ alkylthio groups, C$_6$–C$_{10}$ carbocyclic arylthio groups, C$_1$–C$_6$ alkylsulfonyl groups and C$_6$–C$_{10}$ carbocyclic arylsulfonyl groups wherein the aryl part has from 0 to 3 C$_1$–C$_6$ alkyl substituents; and pharmaceutically acceptable salts and esters thereof.

The invention also provides a pharmaceutical composition for the treatment of angiotensin-induced hypertension, which composition comprises a hypotensive agent in admixture with a pharmaceutically acceptable carrier or diluent, wherein said hypotensive agent is selected from the group consisting of compounds of formula (I) and pharmaceutically acceptable salts and esters thereof.

The invention still further provides a method of treating angiotensin-induced hypertension in a mammal, which may be human or non-human, by administering to said mammal an effective amount of a hypotensive agent, wherein said hypotensive agent is selected from the group consisting of compounds of formula (I) and pharmaceutically acceptable salts and esters thereof.

The invention also provides processes for preparing the compounds of the invention, which are described in more detail hereafter.

DETAILED DESCRIPTION OF INVENTION

The compounds of formula (I) have two free carboxy groups and can thus form mono- or di-esters with appropriate ester-forming groups. There is no practical limitation upon the nature of the ester-forming groups employed in this invention, beyond the practical consideration that, if the resulting compounds are in themselves to be used for the treatment of human beings or other animals, the resulting esters must be "pharmaceutically acceptable"; this, as is well known to the skilled man, means that the ester-forming groups must not, or must not to an unacceptable extent, reduce the activity in vivo or increase the toxicity of the compounds. Where the resulting compounds are not in themselves to be used as medicines but, instead, are to be used as intermediates in the preparation of other compounds, even this practical restriction does not apply and any ester appropriate to the intended preparative route may be formed.

The resulting compounds of the invention may be represented by the formula (Ia):

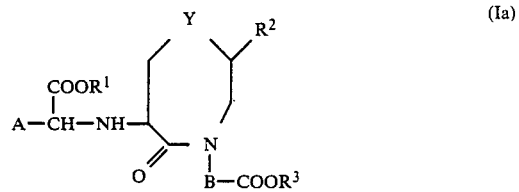

(wherein R$^2$, A, B and Y are as defined above and R$^1$ and R$^3$, which are the same or different, each represents a hydrogen atom or a carboxy-protecting, preferably ester-forming, group).

The carboxy-protecting group represented by R$^1$ and R$^3$ may be any such group known in organic synthesis, although it is preferably an ester residue, especially an ester residue which is capable of easy hydrolysis in vivo (normally in the mammalian body, e.g. blood stream or enteric system) to the free acid, particularly with regard to R$^1$.

Preferably, R$^1$ and R$^3$ are the same or different and each represents a C$_1$–C$_{10}$ alkyl group, an aralkyl group in which the aryl part is a C$_6$–C$_{10}$ carbocyclic aryl group and the alkyl part is C$_1$–C$_6$ alkyl, a C$_6$–C$_{14}$ carbocyclic aryl group, a phthalidyl group or a substituted silyl group, e.g. a trialkylsilyl group where each alkyl part is C$_1$–C$_6$ alkyl, said groups represented by R$^1$ and R$^3$ being unsubstituted or having at least one substituent selected from the group consisting of substituents (a), defined above.

If desired, the alkyl part of the aralkyl group may be attached to two carbon atoms of the aryl group via two of its carbon atoms to form a partially unsaturated, non-aromatic ring (the unsaturation arising from the carbon atoms of the aryl group) through which this aralkyl group is attached to the remainder of the molecule of the compound of formula (I). Alternatively, the aryl group and the alkyl group may be attached to each other through one carbon atom of each group.

Examples of such groups which may be represented by R$^1$ and R$^3$ include:

C$_1$–C$_6$ alkyl groups, such as the methyl, ethyl, propyl, isopropyl, butyl, isobutyl, t-butyl, pentyl and hexyl groups;

aralkyl and diarylalkyl groups, such as the benzyl, benzhydryl (diphenylmethyl), 1-indanyl, 2-indanyl, 1-(1,2,3,4-tetrahydronaphthyl) and 2-(1,2,3,4-tetrahydronaphthyl) groups;

the phthalidyl group;

C$_6$–C$_{10}$ carbocyclic aryl groups, particularly the phenyl group;

trialkylsilyl groups, particularly the trimethylsilyl and t-butyldimethylsilyl groups; and such groups listed above having one or more substituents selected from the group consisting of alkyl, halogen, hydroxy, alkoxy, alkoxyalkoxy, acyloxy, oxo, carboxy, alkoxycarbonyl, alkoxycarbonyloxy, acylamino, nitro, cyano, amino, alkylamino, dialkylamino, arylamino, alkylthio, arylthio, alkylsulfonyl, arylsulfonyl and 2-oxo-1,3-dioxolen-4-yl (which may itself be substituted) substituents.

Where substituents are present, their number is only limited by steric considerations, which depend upon the size of the substituent and of the substituted group; however, in general, from 1 to 3 substituents would be present.

Example of such substituted groups which may be represented by $R^1$ or $R^3$ include halogen-substituted groups, such as the 2,2,2-trichloroethyl and 2-iodoethyl groups; hydroxy-substituted groups, such as the 2-hydroxyethyl and 2,3-dihydroxypropyl groups; alkoxy-substituted groups, such as the methoxymethyl, 2-methoxyethoxymethyl and p-methoxybenzyl groups; acyloxy-substituted groups, such as the acetoxymethyl, 1-acetoxyethyl and pivaloyloxymethyl groups; oxo-substituted groups, such as the phenacyl group; alkoxycarbonyl-substituted groups, such as the methoxycarbonylmethyl and ethoxycarbonylmethyl groups; alkoxycarbonyloxy-substituted groups, such as the ethoxycarbonyloxymethyl and 1-(ethoxycarbonyloxy)ethyl groups; nitro-substituted groups, such as the p-nitrobenzyl group; cyano-substituted groups, such as the 1-cyanoethyl and 2-cyanoethyl groups; alkylthio-substituted groups, such as the methylthiomethyl and ethylthiomethyl groups; arylthio-substituted groups, such as the phenylthiomethyl group; alkylsulfonyl-substituted groups, such as the 2-methanesulfonylethyl and 1-methanesulfonylethyl groups; arylsulfonyl-substituted groups, such as the 2-benzenesulfonylethyl group; and 2-oxo-1,3-dioxolen-4-yl-substituted groups, such as the (5-methyl-2-oxo-1,3-dioxolen-4-yl)methyl and (5-phenyl-2-oxo-1,3-dioxolen-4-yl)methyl groups.

We particularly prefer that $R^1$ and $R^3$ should both represent hydrogen atoms, where the compounds of the present invention are intended for therapeutic use.

However, where the compounds of the present invention are intended for use as intermediate in the preparation of other compounds, we particularly prefer that $R^1$ and $R^3$ should represent a carboxy-protecting group of the type commonly used in organic synthesis, such as a methyl, ethyl, propyl, t-butyl, methoxymethyl, 2,2,2-trichloroethyl, benzyl, p-methoxybenzyl or diphenylmethyl group.

In the compounds of the invention, where $R^2$, $R^4$ or $R^5$ or various substituents, as defined above, are $C_1$–$C_4$ alkyl groups, these groups may be straight or branched chain groups and examples include the methyl, ethyl, propyl, isopropyl, butyl, isobutyl, sec-butyl, t-butyl, pentyl, isopentyl, 2-methylbutyl, neopentyl, t-pentyl, hexyl, 4-methylpentyl, 3-methylpentyl, 2-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and isohexyl groups. In the case of $R^2$, of these we prefer the $C_3$–$C_6$ alkyl groups, particularly the isopropyl, isobutyl, t-butyl, neopentyl and hexyl groups. However, in the case of $R^4$ and $R^5$, we particularly prefer the $C_1$–$C_4$ alkyl groups, particularly the methyl, ethyl, propyl, isopropyl, butyl, isobutyl and sec-butyl groups, the methyl and ethyl groups being more preferred.

Where A represents said group of formula (i) and $R^4$ and/or $R^5$ represents an amino-protecting group, this may be any such group known in organic synthesis. Specific examples include: alkoxycarbonyl groups [in which the alkoxy group may optionally be substituted by one or more of the substituents defined above as substituents (a)], such as the 2,2,2-trichloroethoxycarbonyl, 2-iodoethoxycarbonyl, trimethylsilylethoxycarbonyl, 2-(p-toluenesulfonyl)ethoxycarbonyl, t-butoxycarbonyl, allyloxycarbonyl, benzyloxycarbonyl, p-methoxybenzyloxycarbonyl and p-nitrobenzyloxycarbonyl groups; acyl groups, such as the formyl, acetyl, benzoyl, chloroacetyl and trifluoroacetyl groups; substituted methyl groups, such as the methoxymethyl, benzyloxymethyl, benzyl, 3,4-dimethoxybenzyl or trityl groups; and silyl groups, such as the trimethylsilyl and t-butyldimethylsilyl groups. However, the nature of the amino-protecting group is not critical to the invention, provided that it serves its protecting function.

Where A represents said group of formula (i), Z may represent a $C_1$–$C_8$ alkylene group. The two "free" valencies of the alkylene group may be attached to the same carbon atom (in which case the group is sometimes referred to as an "alkylidene" group) or they may be attached to different carbon atoms. Examples of such alkylene groups which may be represented by Z are the methylene, ethylene, trimethylene, tetramethylene, ethylidene, propylidene, butylidene, pentamethylene, hexamethylene, heptamethylene and octamethylene groups, or such groups having a $C_1$–$C_4$ alkyl substituent, preferably the tetramethylene, pentamethylene, hexamethylene, heptamethylene and octamethylene groups, and most preferably the heptamethylene and octamethylene groups.

Where A represents said group of formula (ii), $R^4$ may be as defined above in relation to the case where A represents said group of formula (i). Where W represents a $C_1$–$C_6$ alkylene group, this may be straight or branched chain, as explained in relation to A, and examples include the methylene, ethylene, trimethylene, tetramethylene, ethylidene, propylidene, butylidene, pentamethylene and hexamethylene groups, of which the ethylene and tetramethylene groups are preferred.

Alternatively, W may represent a a group of formula $-(CH_2)_k-X-(CH_2)_l-$, wherein X represents an oxygen or sulfur atom, k represents the cypher 0 or an integer from 1 to 5 and l represents an integer from 1 to 5. Preferred examples of such groups include the groups of formulae: $-S-(CH_2)_3-$; $-S-(CH_2)_2-$; $-O-(CH_2)_3-$; $-CH_2S(CH_2)_2-$; $-CH_2SCH_2-$; $-CH_2O(CH_2)_2-$; and $-(CH_2)_2SCH_2-$.

Where A represents said group of formula (ii), m and n are the same or different and each is an integer from 1 to 6. Preferably, the sum of m+n is within the range from 3 to 6, and more preferably this sum is from 3 to 5, most preferably 3 or 4, so that the nitrogen-containing heterocycle included in the group of formula (ii) is a pyrolidinyl or piperidyl group, and most preferably a 3-pyrrolidinyl group or a 4-piperidyl group.

Where $R^2$ represents an aryl group, this is a carbocyclic aryl group having from 6 to 10 ring carbon atoms and may be unsubstituted or, if substituted, has at least one substituent selected from the group consisting of substituents (a), defined above. It is preferably a phenyl or naphthyl (1- or 2-naphthyl) group, which is unsubstituted or has at least one $C_1$–$C_4$ alkyl substituent (e.g. a methyl, ethyl, propyl, isopropyl, butyl, isobutyl or t-butyl group). The phenyl group is preferred.

Where $R^2$ represents a cycloalkyl group this contains from 3 to 8, preferably fromm 4 to 6, carbon atoms, and examples include the cyclobutyl, cyclopentyl and cyclohexyl groups.

Where $R^2$ represents a heterocyclic group, this has 5 ring atoms, of which from 1 to 3 are hetero-atoms selected fromm the group consisting of nitrogen, oxygen and sulfur hetero-atoms. Examples of such heterocyclic groups include the furyl, thienyl, imidazolyl, thiazolyl, oxazolyl, isooxazolyl, 1,3,4-oxadiazolyl and 1,3,4-thiadiazolyl groups, which may be unsubstituted or, if substituted, has at least one substituent selected from the group consisting of substituents (a), defined above. It is preferably unsubstituted or has at least one $C_1$–$C_4$ alkyl substituent (e.g. a methyl, ethyl, propyl, isopropyl, butyl, isobutyl or t-butyl group) and/or aryl [e.g. phenyl or naphthyl (1- or 2-naphthyl) group, which is unsubstituted or has at least one $C_1$–$C_4$ alkyl substituent] substituent. More preferably it is unsubstituted or has at least one methyl or phenyl substituent. The most preferred heterocyclic groups are the 2-thienyl, 3-thienyl, 2-furyl, 3-furyl, 4-thiazolyl, 2-methyl-5-thienyl, 3-methyl-2-thienyl, 2-methyl-5-thiazolyl, 2-phenyl-5-thiazolyl and 5-isoxazolyl groups.

B represents a $C_1$–$C_2$ alkylene group, i.e. a methylene or ethylene group, the methylene group being preferred.

Preferred classes of compounds of the present invention are:

(A) Those compounds of formula (I), in which:
A represent a group of formula (i):

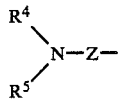
(i)

or a group of formula (ii):

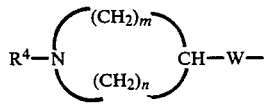
(ii)

in which:
$R^4$ and $R^5$ both represent hydrogen atoms;
Z represents a $C_4$–$C_8$ alkylene group;
W represents a $C_2$–$C_4$ alkylene group or a group of formula $-(CH_2)_k-S-(CH_2)_l-$, wherein k represents the cypher 0 or the integer 1 or 2 and l represents an integer from 1 to 3; and
m and n are the same or different and each represents the integer 1 or 2;
$R^2$ represents a phenyl group, a naphthyl group or a heterocyclic group having 5 ring atoms, of which from 1 to 3 are hetero-atoms selected from the group consisting of nitrogen, oxygen and sulfur atoms, said aryl and heterocyclic groups being unsubstituted or having at least one substituent selected fro the group consisting of substituents (a), defined above;
B represents a methylene group; and
Y represents a sulfur atom or a methylene group;
and pharmaceutically acceptable salts thereof.

(B) Those compounds of formula (I), in which:
A represents a group of formula (i):

(i)

or a group of formula (ii):

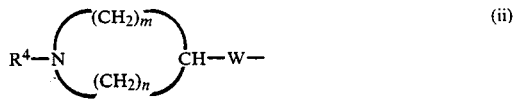
(ii)

in which:
$R^4$ and $R^5$ both represent hydrogen atoms;
Z represents a $C_7$ or $C_8$ alkylene group;
W represents a $C_3$ or $C_4$ alkylene group or a group of formula $-(CH_2)_k-S-(CH_2)_l-$, wherein k represents the cypher 0 or the integer 1 and l represents an integer from 1 to 3;
m represents the integer 1 or 2; and
n represents the integer 2;
$R^2$ represents a phenyl group, a thienyl group, a furyl group, an oxazolyl group, an isoxazolyl group, a thiazolyl group or a 1,3,4-thiadiazolyl group;
B represents a methylene group; and
Y represents a sulfur atom or a methylene group;
and pharmaceutically acceptable salts thereof.

(C) Those compounds of formula (I), in which:
A represents a group of formula $H_2N-Z-$, in which Z represents a $C_7$ or $C_8$ alkylene group;
$R^2$ represents a phenyl group, a 2-thienyl group, a 3-thienyl group or a 2-furyl group;
B represents a methylene group; and
Y represents a sulfur atom or a methylene group;
and pharmaceutically acceptable salts thereof.

(D) Those compounds of formula (I), in which:
A represents a group of formula $H_2N-Z-$, in which Z represents a $C_7$ or $C_8$ alkylene group;
$R^2$ represents a 2-thienyl group, a 3-thienyl group or a 2-furyl group;
B represents a methylene group; and
Y represents a sulfur atom;
and pharmaceutically acceptable salts thereof.

(E) Those compounds of formula (I), in which:
A represents a group of formula (iia):

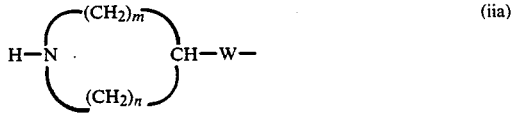
(iia)

in which:
W represents a tetramethylene group or a group of formula $-(CH_2)_k-S-(CH_2)_l-$, wherein k represents the cypher 0 or the integer 1 and l represents an integer from 1 to 3;
m represents the integer 2; and
n represents the integer 2;
$R^2$ represents a phenyl group, a 2-thienyl group, a 3-thienyl group or a 2-furyl group;
B represents a methylene group; and
Y represents a sulfur atom or a methylene group;
and pharmaceutically acceptable salts thereof.

(F) Those compounds of formula (I), in which:
A represents a group of formula (iia):

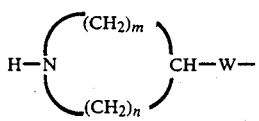

in which:
W represents a tetramethylene group or a group of formula —(CH$_2$)$_k$—S—(CH$_2$)$_l$—, wherein k represents the cypher 0 or the integer 1 and l represents an integer from 1 to 3;
m represents the integer 2; and
n represents the integer 2;
R$^2$ represents a 2-thienyl group, a 3-thienyl group or a 2-furyl group;
B represents a methylene group; and
Y represents a sulfur atom;
and pharmaceutically acceptable salts thereof.

The compounds of formula (I) contain asymmetric carbon atoms at least at the following positions: the carbon atom to which the group of formula —COOR$^1$ is attached; the carbon atom to which the group R$^2$ is attached; and the carbon atom in the perhydrothiazepine or perhydroazepine ring to which the group of formula A—CH(COOH)—NH— is attached; it may also have asymmetric carbon atoms in other positions in some cases, depending upon the nature of the substituents. Accordingly, they may exist as optically pure diastereomers or as mixtures (e.g. racemic mixtures) of diastereomers. Although the various optical isomers are all represented herein by a single formula, the present invention embraces both the individual isolated isomers and mixtures thereof.

The compounds of the invention contain basic nitrogen atoms and hence can form acid addition salts. The nature of such salts is not critical to the present invention, except that, where the salts are to be used for therapeutic purposes, they must be pharmaceutically acceptable which, as is well known to those skilled in the art, means that the salts must not have an increased toxicity (or an unacceptably increased toxicity) or a reduced activity (or unacceptably reduced activity) as compared with the free bases. A wide variety of acids may be employed to form such salts and representative examples of such acids include: mineral acids, such as the hydrohalic acids (e.g. hydrochloric acid, hydrobromic acid and hydroiodic acid), phosphoric acid, metaphosphoric acid, nitric acid or sulfuric acid; and organic carboxylic acids, such as acetic acid, oxalic acid, tartaric acid, citric acid, benzoic acid, glycolic acid, gluconic acid, glucuronic acid, succinic acid, maleic acid or fumaric acid; and organic sulfonic acids, such as methanesulfonic acid, benzenesulfonic acid or p-toluenesulfonic acid. Such acid addition salts may be prepared by conventional methods.

The compounds of the invention may also contain 2 free carboxy groups, and these may form salts with bases. Examples of salts with bases include: salts with metals, especially alkali metals and alkaline earth metals, such as the lithium, sodium, potassium, calcium and magnesium salts; the ammonium salt; salts with organic amines, such as cyclohexylamine, dicyclohexylamine, diisopropylamine, triethylamine, cinchonine, guanidine or guanine; and salts with basic amino acids, such as lysine or arginine.

Examples of specific compounds of the invention are given in the following formulae (I-1) to (I-5), in which the substituents are as defined in the corresponding one of Table 1 to 5 [i.e. Table 1 relates to formula (I-1). Table 2 relates to formula (I-2) and so on]. The compounds of the invention are hereinafter, where appropriate, identified by the numbers appended to them in these Tables. In the Tables, the following abbreviations are used:

| | |
|---|---|
| Ac | acetyl |
| Boc | t-butoxycarbonyl |
| Bu | butyl |
| tBu | t-butyl |
| Bz | benzyl |
| Bzo | benzoyl |
| Cbz | benzyloxycarbonyl |
| Dox | (5-methyl-2-oxo-1,3-dioxolen-4-yl)methyl |
| Et | ethyl |
| Etc | ethoxycarbonyl |
| Fur | furyl |
| cHx | cyclohexyl |
| Isox | isoxazolyl |
| Me | methyl |
| Np | naphthyl |
| Ph | phenyl |
| Phtm | phthalimido |
| Piv | pivaolyl |
| cPn | cyclopentyl |
| iPr | isopropyl |
| Thi | thienyl |
| Thiz | thiazolyl |

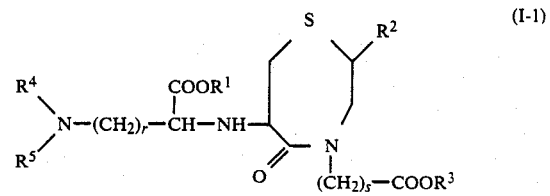

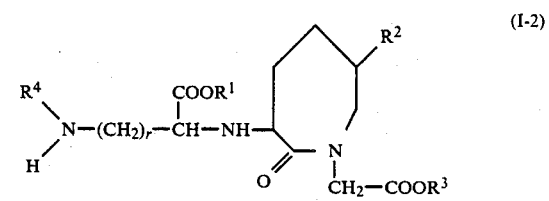

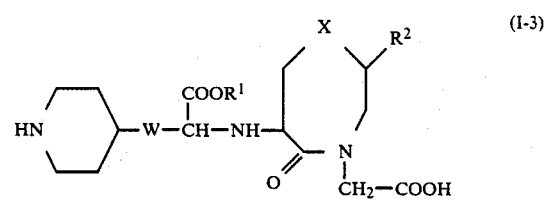

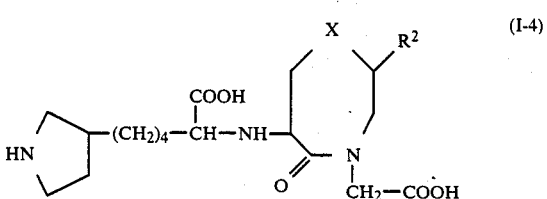

-continued

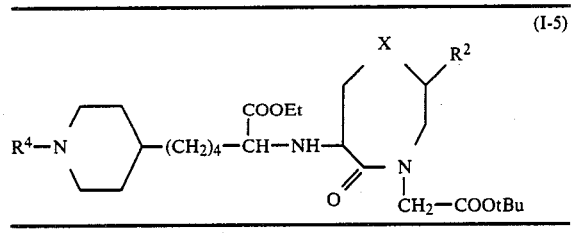
(I-5)

TABLE 1

| Cpd. No. | —NR⁴R⁵ | r | R¹ | R² | s | R³ |
|---|---|---|---|---|---|---|
| 1-1 | NH₂ | 3 | H | 2-Thi | 1 | H |
| 1-2 | NH₂ | 3 | Et | 2-Thi | 1 | H |
| 1-3 | NH₂ | 4 | H | 2-Thi | 1 | H |
| 1-4 | NH₂ | 4 | Et | 2-Thi | 1 | H |
| 1-5 | NH₂ | 5 | H | 2-Thi | 1 | H |
| 1-6 | NH₂ | 5 | Et | 2-Thi | 1 | H |
| 1-7 | NH₂ | 6 | H | 2-Thi | 1 | H |
| 1-8 | NH₂ | 6 | Et | 2-Thi | 1 | H |
| 1-9 | NH₂ | 6 | Bu | 2-Thi | 1 | H |
| 1-10 | NH₂ | 6 | Bz | 2-Thi | 1 | H |
| 1-11 | NH₂ | 7 | H | 2-Thi | 1 | H |
| 1-12 | NH₂ | 7 | Et | 2-Thi | 1 | H |
| 1-13 | NH₂ | 8 | H | 2-Thi | 1 | H |
| 1-14 | NH₂ | 5 | H | 3-Thi | 1 | H |
| 1-15 | NH₂ | 5 | Et | 3-Thi | 1 | H |
| 1-16 | NH₂ | 6 | H | 3-Thi | 1 | H |
| 1-17 | NH₂ | 6 | Et | 3-Thi | 1 | H |
| 1-18 | NH₂ | 7 | H | 3-Thi | 1 | H |
| 1-19 | NH₂ | 7 | Et | 3-Thi | 1 | H |
| 1-20 | NH₂ | 5 | H | 2-Fur | 1 | H |
| 1-21 | NH₂ | 5 | Et | 2-Fur | 1 | H |
| 1-22 | NH₂ | 6 | H | 2-Fur | 1 | H |
| 1-23 | NH₂ | 6 | Et | 2-Fur | 1 | H |
| 1-24 | NH₂ | 7 | H | 2-Fur | 1 | H |
| 1-25 | NH₂ | 7 | Et | 2-Fur | 1 | H |
| 1-26 | NH₂ | 5 | H | 4-Thiz | 1 | H |
| 1-27 | NH₂ | 5 | Et | 4-Thiz | 1 | H |
| 1-28 | NH₂ | 6 | H | 4-Thiz | 1 | H |
| 1-29 | NH₂ | 6 | Et | 4-Thiz | 1 | H |
| 1-30 | NH₂ | 7 | H | 4-Thiz | 1 | H |
| 1-31 | NH₂ | 7 | Et | 4-Thiz | 1 | H |
| 1-32 | NH₂ | 6 | H | 5-Me—2-Thi | 1 | H |
| 1-33 | NH₂ | 6 | Et | 5-Me—2-Thi | 1 | H |
| 1-34 | NH₂ | 6 | H | 3-Me—2-Thi | 1 | H |
| 1-35 | NH₂ | 7 | H | 3-Me—2-Thi | 1 | H |
| 1-36 | NH₂ | 6 | Et | 3-Me—2-Thi | 1 | H |
| 1-37 | NH₂ | 6 | H | 2-Me—5-Thiz | 1 | H |
| 1-38 | NH₂ | 6 | Et | 2-Me—5-Thiz | 1 | H |
| 1-39 | NH₂ | 6 | H | 2-Ph—5-Thiz | 1 | H |
| 1-40 | NH₂ | 6 | Et | 2-Ph—5-Thiz | 1 | H |
| 1-41 | BocNH— | 6 | H | 2-Thi | 1 | H |
| 1-42 | BocNH— | 6 | Et | 2-Thi | 1 | H |
| 1-43 | BocNH— | 6 | Et | 2-Thi | 1 | tBu |
| 1-44 | BocNH— | 7 | Et | 2-Thi | 1 | tBu |
| 1-45 | CbzNH— | 6 | H | 2-Thi | 1 | H |
| 1-46 | CbzNH— | 6 | Et | 2-Thi | 1 | H |
| 1-47 | AcNH— | 6 | H | 2-Thi | 1 | H |
| 1-48 | AcNH— | 6 | Et | 2-Thi | 1 | H |
| 1-49 | BzoNH— | 6 | H | 2-Thi | 1 | H |
| 1-50 | BzoNH— | 6 | Et | 2-Thi | 1 | H |
| 1-51 | Phtm | 6 | H | 2-Thi | 1 | H |
| 1-52 | Phtm | 6 | Et | 2-Thi | 1 | H |
| 1-53 | NH₂ | 6 | Et | 2-Thi | 1 | PivMe |
| 1-54 | NH₂ | 6 | Et | 2-Thi | 1 | 1-EtcOEt |
| 1-55 | NH₂ | 6 | Et | 2-Thi | 1 | Dox |
| 1-56 | Phtm | 4 | tBu | 2-Thi | 1 | tBu |
| 1-57 | NH₂ | 6 | Et | 2-Thi | 2 | H |
| 1-58 | NH₂ | 6 | H | 2-Thi | 2 | H |
| 1-59 | NH₂ | 6 | H | Me | 1 | H |
| 1-60 | NH₂ | 6 | Et | Me | 1 | H |
| 1-61 | NH₂ | 6 | H | iPr | 1 | H |
| 1-62 | NH₂ | 6 | Et | iPr | 1 | H |
| 1-63 | NH₂ | 6 | H | Ph | 1 | H |
| 1-64 | NH₂ | 6 | Et | Ph | 1 | H |
| 1-65 | BocNH— | 6 | Et | Ph | 1 | tBu |
| 1-66 | NH₂ | 4 | tBu | 2-Thi | 1 | tBu |

TABLE 1-continued

| Cpd. No. | —NR⁴R⁵ | r | R¹ | R² | s | R³ |
|---|---|---|---|---|---|---|
| 1-67 | Phtm | 4 | Et | Ph | 1 | tBu |
| 1-68 | Phtm | 4 | Et | Ph | 1 | H |
| 1-69 | NH₂ | 5 | H | Ph | 1 | H |
| 1-70 | NH₂ | 5 | Et | Ph | 1 | H |
| 1-71 | NH₂ | 7 | H | Ph | 1 | H |
| 1-72 | NH₂ | 7 | Et | Ph | 1 | H |
| 1-73 | NH₂ | 6 | H | 2-Np | 1 | H |
| 1-74 | NH₂ | 6 | Et | 2-Np | 1 | H |
| 1-75 | NH₂ | 6 | H | 1-Np | 1 | H |
| 1-76 | NH₂ | 6 | Et | 1-Np | 1 | H |
| 1-77 | MeNH— | 6 | H | 2-Thi | 1 | H |
| 1-78 | MeNH— | 6 | Et | 2-Thi | 1 | H |
| 1-79 | AcN(Me)— | 6 | H | 2-Thi | 1 | H |
| 1-80 | AcN(Me)— | 6 | Et | 2-Thi | 1 | H |
| 1-81 | EtNH— | 6 | H | 2-Thi | 1 | H |
| 1-82 | EtNH— | 6 | Et | 2-Thi | 1 | H |
| 1-83 | Me₂N— | 6 | H | 2-Thi | 1 | H |
| 1-84 | Me₂N— | 6 | Et | 2-Thi | 1 | H |
| 1-85 | Et₂N— | 6 | H | 2-Thi | 1 | H |
| 1-86 | Et₂N— | 6 | Et | 2-Thi | 1 | H |

TABLE 2

| Cpd. No. | R⁴ | r | R¹ | R² | R³ |
|---|---|---|---|---|---|
| 2-1 | H | 4 | H | 2-Thi | H |
| 2-2 | H | 4 | Et | 2-Thi | H |
| 2-3 | H | 5 | H | 2-Thi | H |
| 2-4 | H | 5 | Et | 2-Thi | H |
| 2-5 | H | 6 | H | 2-Thi | H |
| 2-6 | H | 6 | Et | 2-Thi | H |
| 2-7 | H | 7 | H | 2-Thi | H |
| 2-8 | H | 7 | Et | 2-Thi | H |
| 2-9 | H | 8 | H | 2-Thi | H |
| 2-10 | H | 8 | Et | 2-Thi | H |
| 2-11 | Boc | 6 | H | 2-Thi | H |
| 2-12 | Boc | 6 | Et | 2-Thi | H |
| 2-13 | H | 4 | H | Ph | H |
| 2-14 | H | 4 | Et | Ph | H |
| 2-15 | H | 5 | H | Ph | H |
| 2-16 | H | 5 | Et | Ph | H |
| 2-17 | H | 6 | H | Ph | H |
| 2-18 | H | 6 | Et | Ph | H |
| 2-19 | H | 7 | H | Ph | H |
| 2-20 | H | 7 | Et | Ph | H |
| 2-21 | H | 8 | H | Ph | H |
| 2-22 | H | 8 | Et | Ph | H |
| 2-23 | Boc | 6 | Et | Ph | H |
| 2-24 | Boc | 6 | Et | Ph | tBu |
| 2-25 | Boc | 7 | Et | Ph | tBu |

TABLE 3

| Cpd. No. | W | R¹ | R² | X |
|---|---|---|---|---|
| 3-1 | —(CH₂)₄— | H | 2-Thi | S |
| 3-2 | —(CH₂)₄— | Et | 2-Thi | S |
| 3-3 | —(CH₂)₄— | Bu | 2-Thi | S |
| 3-4 | —(CH₂)₄— | Bz | 2-Thi | S |
| 3-5 | —(CH₂)₄— | H | Ph | S |
| 3-6 | —(CH₂)₄— | Et | Ph | S |
| 3-7 | —(CH₂)₄— | H | 3-Thi | S |
| 3-8 | —(CH₂)₄— | H | 2-Fur | S |
| 3-9 | —(CH₂)₄— | H | 3-Fur | S |
| 3-10 | —(CH₂)₄— | H | 4-Thiz | S |
| 3-11 | —(CH₂)₄— | H | 5-Me—2-Thi | S |
| 3-12 | —(CH₂)₄— | H | 3-Me—2-Thi | S |
| 3-13 | —(CH₂)₄— | H | 2-Ph—5-Thiz | S |
| 3-14 | —(CH₂)₄— | H | 5-Isox | S |
| 3-15 | —(CH₂)₄— | H | 2-Np | S |
| 3-16 | —(CH₂)₄— | H | 1-Np | S |
| 3-17 | —(CH₂)₄— | H | 2-Thi | CH₂ |
| 3-18 | —(CH₂)₄— | Et | 2-Thi | CH₂ |
| 3-19 | —(CH₂)₄— | H | 3-Thi | CH₂ |
| 3-20 | —(CH₂)₄— | H | Ph | CH₂ |
| 3-21 | —(CH₂)₄— | Et | Ph | CH₂ |
| 3-22 | —(CH₂)₄— | H | 2-Np | CH₂ |

TABLE 3-continued

| Cpd. No. | W | R¹ | R² | X |
|---|---|---|---|---|
| 3-23 | —(CH₂)₄— | H | 1-Np | CH₂ |
| 3-24 | —(CH₂)₃— | H | 2-Thi | S |
| 3-25 | —(CH₂)₃— | H | Ph | S |
| 3-26 | —(CH₂)₃— | H | Ph | CH₂ |
| 3-27 | —(CH₂)₅— | H | 2-Thi | S |
| 3-28 | —(CH₂)₅— | H | Ph | S |
| 3-29 | —(CH₂)₅— | H | Ph | CH₂ |
| 3-30 | —(CH₂)₂— | H | 2-Thi | S |
| 3-31 | —(CH₂)₂— | H | Ph | S |
| 3-32 | —(CH₂)₂— | H | Ph | CH₂ |
| 3-33 | —S—(CH₂)₃— | H | 2-Thi | S |
| 3-34 | —S—(CH₂)₃— | H | Ph | S |
| 3-35 | —S—(CH₂)₃— | H | Ph | CH₂ |
| 3-36 | —S—(CH₂)₂— | H | 2-Thi | S |
| 3-37 | —S—(CH₂)₂— | H | Ph | S |
| 3-38 | —S—(CH₂)₂— | H | Ph | CH₂ |
| 3-39 | —O—(CH₂)₂— | H | 2-Thi | S |
| 3-40 | —O—(CH₂)₃— | H | Ph | S |
| 3-41 | —O—(CH₂)₃— | H | Ph | CH₂ |
| 3-42 | —CH₂S(CH₂)₂— | H | 2-Thi | S |
| 3-43 | —CH₂S(CH₂)₂— | H | Ph | S |
| 3-44 | —CH₂S(CH₂)₂— | H | Ph | CH₂ |
| 3-45 | —CH₂SCH₂— | H | 2-Thi | S |
| 3-46 | —CH₂SCH₂— | H | Ph | S |
| 3-47 | —CH₂SCH₂— | H | Ph | CH₂ |
| 3-48 | —CH₂O(CH₂)₂— | H | 2-Thi | S |
| 3-49 | —CH₂O(CH₂)₂— | H | Ph | S |
| 3-50 | —CH₂O(CH₂)₂— | H | Ph | CH₂ |
| 3-51 | —(CH₂)₂SCH₂— | H | 2-Thi | S |
| 3-52 | —(CH₂)₂SCH₂— | H | Ph | S |
| 3-53 | —(CH₂)₂SCH₂— | H | Ph | CH₂ |
| 3-54 | —(CH₂)₄— | H | iPr | S |
| 3-55 | —(CH₂)₄— | H | iPr | CH₂ |
| 3-56 | —(CH₂)₄— | H | Me | S |
| 3-57 | —(CH₂)₄— | H | Me | CH₂ |
| 3-58 | —(CH₂)₄— | Et | cPn | S |
| 3-59 | —(CH₂)₄— | H | cPn | S |
| 3-60 | —(CH₂)₄— | Et | cHx | CH₂ |
| 3-61 | —(CH₂)₄— | H | cHx | CH₂ |

TABLE 4

| Cpd. No. | R² | X |
|---|---|---|
| 4-1 | 2-Thi | S |
| 4-2 | 2-Thi | CH₂ |
| 4-3 | Ph | S |
| 4-4 | Ph | CH₂ |

TABLE 5

| Cpd. No. | R⁴ | R² | X |
|---|---|---|---|
| 5-1 | Boc | 2-Thi | S |
| 5-2 | Boc | Ph | S |
| 5-3 | Boc | Ph | CH₂ |
| 5-4 | CBz | 2-Thi | S |
| 5-5 | CBz | Ph | S |
| 5-6 | CBz | Ph | CH₂ |

Of the compounds listed above, the following are preferred in view of their excellent ACE inhibitory activity: Compounds Nos. 1-3, 1-5, 1-7, 1-11, 1-13 1-16, 1-18, 1-22, 1-24, 1-30, 1-63, 1-71, 2-1, 2-1, 2-3, 2-5, 2-7, 2-9, 2-19, 2-21, 3-1, 3-5, 3-7, 3-8, 3-17, 3-19, 3-20, 3-33, 3-35, 3-36, 3-42, 3-43, 4-1, 4-2, 4-3, and 4-4. The following, although effective ACE inhibitors, are of more value as intermediates in the preparation of other, and more valuable, ACE inhibitors and are preferred in view of their use as intermediates: Compounds Nos. 1-8, 1-12, 1-43, 1-44, 1-56, 1-64, 1-65, 1-66, 2-8, 2-10, 2-20, 2-25, 3-2, 5-1, 5-2 and 5-3.

The following compounds, in view of their exceptional ACE inhibitory activity, are most preferred:

1-11. α-[6-(8-Amino-1-carboxyoctylamino)-5-oxo-2-(2-thienyl)perhydro-1,4-thiazepin-4-yl]acetic acid.

1-13. α-[6-(9-Amino-1-carboxynonylamino)-5-oxo-2-(2-thienyl)perhydro-1,4-thiazepin-4-yl]acetic acid.

1-18. α-[6-(8-Amino-1-carboxyoctylamino)-5-oxo-2-(3-thienyl)perhydro-1,4-thiazepin-4-yl]acetic acid.

1-24. α-[6-(8-Amino-1-carboxyoctylamino)-5-oxo-2-(2-furyl)perhydro-1,4-thiazepin-4-yl]acetic acid.

1-71. α-[(6-(8-Amino-1-carboxyoctylamino)-5-oxo-2-phenyl-perhydro-1,4-thiazepin-4-yl]acetic acid.

2-7. α-[3-(8-Amino-1-carboxyoctylamino)-2-oxo-6-(2-thienyl)perhydroazepin-1-yl]acetic acid.

2-9. α-[3-(9-Amino-1-carboxynonylamino)-2-oxo-6-(2-thienyl)perhydroazepin-1-yl]acetic acid.

2-19. α-[3-(8-Amino-1-carboxyoctylamino)-2-oxo-6-phenyl-perhydroazepin-1-yl]acetic acid.

2-21. α-[3-(9-Amino-1-carboxynonylamino)-2-oxo-6-phenyl-perhydroazepin-1-yl]acetic acid.

3-1. α-{6-[1-Carboxy-5-(4-piperidyl)pentylamino]-5-oxo-2-(2-thienyl)perhydro-1,4-thiazepin-4-yl}acetic acid.

3-5. α-{6-[1-Carboxy-5-(4-piperidyl)pentylamino]-5-oxo-2-phenylperhydro-1,4-thiazepin-4yl]acetic acid.

3-7. α-{6-[1-Carboxy-5-(4-piperidyl)pentylamino]-5-oxo-2-(3-thienyl)perhydro-1,4-thiazepin-4-yl]acetic acid.

3-8. α-{6-[1-Carboxy-5-(4-piperidyl)pentylamino]-5-oxo-2-(2-furyl)perhydro-1,4-thiazepin-4-yl]acetic acid.

3-17. α-{3-[1-Carboxy-5-(4-piperidyl)pentylamino]-2-oxo-6-(2-thienyl)perhydroazepin-1-yl}acetic acid.

3-19. α-{3-[1-Carboxy-5-(4-piperidyl)pentylamino]-2-oxo-6-(3-thienyl)perhydroazepin-1-yl}acetic acid.

3-20. α-{3-[1-Carboxy-5-(4-piperidyl)pentylamino]-9-oxo-6-phenylperhydroazepin-1-yl}acetic acid.

In particular, the following isomers of certain of the above most preferred compounds are preferred:

1.11. α-o6(R)-[8-Amino-1(S)-carboxyoctylamino]-5-oxo-2(S)-(2-thienyl)perhydro-1,4-thiazepin-4-yl}acetic acid.

2-19. α-{3(S)-[8-Amino-1(S)-carboxyoctylamino]-2-oxo-6(R)-phenylperhydroazepin-1-yl}acetic acid.

3-1. α-{6(R)-[1(S)-Carboxy-5-(4-piperidyl)pentylamino]-5-oxo-2(S)-(2-thienyl)perhydro-1,4-thiazepin-4-yl}acetic acid.

3-20. α-{3(S)-[1(S)-Carboxy-5-(4-piperidyl)pentylamino]-2-oxo-6(R)-phenylperhydroazepin-1-yl}acetic acid.

The compounds of the present invention can be prepared by the condensation of a compound of formula (II):

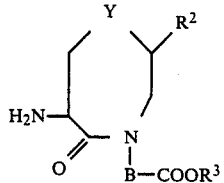  (II)

(in which R², R³, B and Y are as defined above) with a compound of formula (III):

A—CH(COOR¹)—X'  (III)

(in which R¹ and A are as defined above and X' represents a halogen atom or a sulfonyloxy group) or by reductive condensation of the aforementioned compound of formula (II) with a compound of formula (IV):

A—C(=O)—COOR¹    (IV)

(in which R¹ and A are as defined above).

In the compound of formula (III), where X' represents a halogen atom, this is preferably a chlorine, bromine or iodine atom; where X' represents a sulfonyloxy group, this is preferably a substituted or unsubstituted $C_1$–$C_6$ alkanesulfonyloxy group, such as a methanesulfonyloxy, ethanesulfonyloxy or trifluoromethanesulfonyloxy group, or a substituted or unsubstituted aromatic sulfonyloxy group, such as a benzenesulfonyloxy, p-toluenesulfonyloxy, p-nitrobenzenesulfonyloxy, o-nitrobenzenesulfonyloxy, m-nitrobenzenesulfonyloxy, 2,4-dinitrobenzenesulfonyloxy, 2-methyl-5-nitrobenzenesulfonyloxy, 4-chloro-3-nitrobenzenesulfonyloxy, p-bromobenzenesulfonyloxy, p-chlorobenzenesulfonyloxy or 2,5-dichlorobenzenesulfonyloxy group; in the case of the substituted groups, substituents are selected from the group consisting of substituents (a) defined above.

Condensation of the compound of formula (II) with the compound of formula (III) is preferably effected in the presence of a solvent and of a base. The nature of the solvent is not critical, provided that it has no adverse effect upon the reaction; suitable solvents include: aliphatic and aromatic hydrocarbons, such as hexane or benzene; halogenated aliphatic or aromatic, preferably aliphatic, hydrocarbons, such as methylene chloride, chloroform or 1,2-dichloroethane; ethers, such as tetrahydrofuran or dioxane; esters, such as ethyl acetate; ketones, such as acetone; amides, such as dimethylformamide, dimethylacetamide, N-methyl-2-pyrrolidone or hexamethylphosphoric triamide; sulfoxides, such as dimethyl sulfoxide; and nitriles, such as acetonitrile. There is likewise no criticality as to the nature of the base to be employed, provided that it does not adversely affect the reaction. Suitable bases include, for example: alkali metal and alkaline earth metal carbonates, such as sodium carbonate, potassium carbonate or calcium carbonate; alkali metal bicarbonates, such as sodium bicarbonate or potassium bicarbonate; alkali metal hydrides, such as sodium hydride or lithium hydride; metal, especially alkali metal, fluorides, such as potassium fluoride or cesium fluoride; and organic bases, such as triethylamine, pyridine, picoline or tetraethylammonium hydroxide. If desired, the reaction may be carried out in a two-phase reaction system employing water as the solvent for one phase and a water-immiscible solvent (such as methylene chloride or chloroform) for the other phase; in this case, a phase-transfer catalyst (such as tetrabutylammonium bromide or benzyltriethylammonium iodide) should be employed and the base may be a relatively strong base, such as an alkali metal hydroxide (for example sodium hydroxide or potassium hydroxide).

The reaction will take place over a wide range of temperatures and the precise temperature chosen is not critical to the present invention; we generally find it convenient to carry out the reaction at a temperature within the range from 0° to 120° C. The time required for the reaction will vary depending upon many factors, but primarily upon the natures of the solvent, base and reagents, and upon the reaction temperature, but a period of from 1 hour to 3 days will normally suffice.

After completion of the reaction, the desired compound may be obtained from the reaction mixture by conventional means. For example, one suitable recovery technique comprises: adding an organic solvent, such as ethyl acetate, to the reaction mixture; separating the organic layer and washing it with water; drying the organic layer; and distilling off the solvent to give the desired product. If necessary, this product can be further purified by various conventional techniques, such as recrystallization and/or the chromatography techniques, particularly column chromatography.

Reaction of the compound of formula (II) with the compound of formula (IV) takes place under reductive condensation conditions. The reductive conditions may be provided by a variety of means, for example: catalytic reduction using a metal, such as platinum, palladium, Raney nickel or rhodium, optionally on a carrier, in the presence of hydrogen; reduction with a metal hydride, such as lithium aluminum hydride, lithium borohydride, lithium cyanoborohydride, sodium cyanoborohydride, sodium borohydride or potassium borohydride; reduction with an active metal, such as sodium or magnesium, together with an alcohol, such as methanol or ethanol; or reduction with a metal, such as iron or zinc, and an acid, such as hydrochloric acid or acetic acid. The reaction is preferably effected in the presence of a solvent, the nature of which is not critical, provided that it has no adverse effect upon (although it may participate in) the reaction. Suitable solvents include water and a variety of organic solvents, for example: alcohols, such as methanol or ethanol; ethers, such as tetrahydrofuran, diethyl ether or dioxane; halogenated hydrocarbons, particularly halogenated aliphatic hydrocarbons, such as methylene chloride or chloroform; esters, such as ethyl acetate; aromatic hydrocarbons, such as benzene or toluene; amides, such as dimethylformamide or dimethylacetamide; and organic carboxylic acids, such as acetic acid. It will be noted that certain of the compounds mentioned herein as potential solvents may also serve as part of the reduction system described above and, in that case, the same compound may serve both as a reagent and as a solvent, if desired.

The reaction will take place over a wide range of temperatures, for example from −20° C. to +100° C., although the precise temperature chosen will depend upon several factors, of which the most important is the nature of the reductive system employed. The reaction can be carried out under atmospheric pressure, although, in some cases, it may be desirable to carry it out under an elevated or reduced pressure.

If it is desired to prepared a compound of formula (I) in which $R^4$ and/or $R^5$ represents a hydrogen atom, it is preferable that the corresponding group in the compound of formula (II) should be protected, although it may not be necessary in all cases that both $R^4$ and $R^5$ should be protected if A represents a group of formula —$NR^4R^5$. In this case, the protecting group may be any one of those described above, and it may be removed by conventional means well known in this field, for example treatment with an acid or an alkali or by reduction, depending on the nature of the protecting group.

Of the compounds of formula (I), the dicarboxylic acids in which both $R^1$ and $R^3$ represent hydrogen atoms, as well as the salts of these acids, are medically the most important compounds.

A dicarboxylic acid of formula (I) in which both $R^1$ and $R^3$ represent hydrogen atoms can be prepared by hydrolyzing a diester or monoester of formula (I) (in which $R^1$ and $R^3$ represent ester residues or $R^1$ represents an ester residue and $R^3$ represents a hydrogen atom) with an acid or base; it may also be prepared by reductive removal of the ester group or groups of the diester or monoester, or (when the compound contains an allyl ester group) catalytic removal of the allyl group with a suitable catalyst such as tetrakis(triphenylphosphine)palladium (O). The reaction conditions employed are the same as those used conventionally for reactions of this type and are well known to those skilled in the art.

In the compounds of the invention, there may be present several asymmetric carbon atoms. Hence, various diastereoisomers are possible, as described above. If necessary, these diastereoisomers may be separated by chromatography or fractional recrystallization. Alternatively, the individual isomers may be prepared by starting from an individual isomer of the starting material of formula (II), which itself may have been obtained by appropriate resolution or separation tequniques. If at least one of the starting materials is a mixture of isomers, the compound of the invention is normally likewise obtained as a mixture of isomers. If desired, this mixture of optical isomers may be separated by conventional resolution methods, for example the formation of salts with optically active bases, such as cinchonine, cinchonidine, quinine or quinidine, or with optically active organic acids, e.g. l-camphorsulfonic acid or d-camphorsulfonic acid. Optical isomers can also be resolved by other known techniques, including various kinds of chromatography, fractional crystallization etc.

The compounds of formula (II) used as starting materials may be obtained by various well known routes, for example as described in U.S. patent application Ser. No. 721 303 and U.S. patent application Ser. No. 917,041.

As noted above, the compounds of the present invention have the ability to inhibit the activity of ACE, the enzyme which converts angiotensin I to angiotensin II and also inactivates bradykinin. The physiological activity of the compounds of the invention can be evaluated by determining the concentration of the test compound required to inhibit the activity of ACE by 50% in vitro ($IC_{50}$), for example by the procedure of D. W. Cushman et al. [Biochemical Pharmacology, 20, 1637 (1971)]. Specifically, solutions of ACE extracted from rabbit lungs and, as substrate, hippurylhistidylleucine, to which had been added the test compound at various concentrations, were added to a borate buffer solution containing sodium chloride, and the pH was adjusted to a value of 8.3. The enzymatic reaction was allowed to proceed at 37° C. for 30 minutes, after which time the reaction was terminated by adding 1N aqueous hydrochloric acid. The hippuric acid formed by this reaction was extracted with ethyl acetate and the solvent was then distilled from the extract. The residual hippuric acid was dissolved in water. The amount of hippuric acid in the resulting aqueous solution was determined by the absorbency to ultraviolet radiation at 228 nm. The resulting values were then plotted to form a curve indicating the relationship between the amount of hippuric acid formed and the concentration of the test compound. The $IC_{50}$ value can be obtained by reading on this curve the concentration of the test compound which reduces the amount of hippuric acid formed to one half of that formed when no test compound is present. The $IC_{50}$ values obtained for varius of the compounds of the invention by this procedure are shown in the following Table 6. The compounds tested were as follows:

A: α-{6(R)-[5-Amino-1(S)-carboxypentylamino]-5-oxo-2(S)-(2-thienyl)perhydro-1,4-thiazepin-4-yl}acetic acid dihydrochloride (product of Example 3);

B: α-{6(R)-[7-Amino-1(S)-carboxyheptylamino]-5-oxo-2(S)-(2-thienyl)perhydro-1,4-thiazepin-4-yl}acetic acid (product of Example 6);

C: rel-α-}6(R)-[7-Amino-1(S)-carboxyheptylamino]-5-oxo-2(R)-phenylperhydro-1,4-thiazepin-4-yl}acetic acid (product of Example 9).

D: α-{(6(R)-[8-Amino-1(S)-carboxyoctylamino]-5-oxo-2(S)-(2-thienyl)perhydro-1,4-thiazepin-4-yl}acetic acid (product of Example 14).

E: rel-α-{3(S)-[8-Amino-1(S)-carboxyoctylamino]-2-oxo-6(R)-phenylperhydrozepin-1-yl}acetic acid (product of Example 17).

F: α-{6(R)-[1(S)-Carboxy-5-(4-piperidyl)pentylamino]-5-oxo-2(S)-(2-thienyl)perhydro-1,4-thiazepin-4-yl}acetic acid (product of Example 20).

G: rel-α-{3(S)-[1(S)-Carboxy-5-(4-piperidyl)pentylamino]-2-oxo-6(R)-phenylperhydroazepin-1-yl}acetic acid (product of Example 23).

TABLE 6

| Test Compound | $IC_{50}$ (moles/liter) |
| --- | --- |
| A | $3.3 \times 10^{-9}$ |
| B | $2.0 \times 10^{-9}$ |
| C | $3.1 \times 10^{-9}$ |
| D | $1.6 \times 10^{-9}$ |
| E | $4.1 \times 10^{-9}$ |
| F | $1.6 \times 10^{-9}$ |
| G | $3.7 \times 10^{-9}$ |

As can be clearly seen from the results in the above Table, the compounds of the inventon inhibit ACE activity at very low concentrations and are thus useful as diagnostic, preventative and therapeutic agents for hypertensive patients; likewise, salts of these compounds would have similar activities.

For practical, therapeutic use, the compounds of the invention are preferably administered in combination with suitable pharmaceutically acceptable carriers, vehicles or diluents. The compounds can be administered orally or non-orally (e.g. parenterally by intravenous or intramuscular injection) and the form of the composition will, of course, be determined by the intended route of administration. For oral administration, the compounds of the invention may, for example, be administered as powders, granules, tablets, capsules, syrups or elixirs. For parenteral administration, the compounds will be administered in the form of a suitable injectable composition, in which the compound of the invention is dissolved or suspended in a pyrogen-free injectable medium. The dose will vary depending upon the nature and severity of the disorder, as well as upon the age, condition and body weight of the patient. For example, for the therapy of an adult human patient, the dose at each administration would preferably be from 0.5 to 1000 mg, more preferably from 1 to 100 mg, for oral administration, whilst the preferred dose at each administration for intravenous injection is from 0.1 to 100 mg, more preferably from 0.1 to 10 mg. One or more of these doses, preferably from 1 to 3 doses, may be administered daily.

The invention is further illustrated by the following Examples, which describe the preparation of various compounds of the invention. The values for optical rotation were all measured with the sodium D-line, i.e. all values are $[=]_D$.

EXAMPLE 1 t-Butyl α-[6(R)-(1-t-butoxycarbonyl-5-phthalimidopentylamino)-5-oxo-2(S)-(2-thienyl)perhydro-1,4-thiazepin-4-yl]acetate 3 g of sodium carbonate were added to a solution of 1.35 g of t-butyl α-[6(R)-amino-5-oxo-2(S)-(2-thienyl)-perhydro-1,4-thiazepin-4-yl]acetate and 2.23 g of t-butyl 2-bromo-6-phthalimidohexanoate dissolved in 20 ml of dimethylformamide, and the mixture was stirred at 60° C. for 24 hours. The reaction mixture was then mixed with a mixture of ethyl acetate and water. The ethyl acetate layer was separated, washed with an aqueous solution of sodium chloride, dried over anhydrous magnesium sulfate and concentrated by evaporation under reduced pressure to remove the solvent. The residue was subjected to column chromatography through silica gel using a 5:1 by volume mixture of cyclohexane and ethyl acetate as the eluent.

700 mg of t-butyl α-{6(R)-[1(R)-t-butoxycarbonyl-5-phthalimidopentylamino]-5-oxo-2(S)-(2-thienyl)perhydro-1,4-thiazepin-4-yl}acetate were obtained as a foamy solid from the fractions first eluted.

Nuclear Magnetic Resonance Spectrum (CDCl$_3$) δ ppm: 1.48 (18H, singlet); 1.0–2.0 (6H, multiplet); 2.4–4.8 (12H, multiplet); 6.85–7.3 (3H, multiplet); 7.55–8.0 (4H, multiplet).

Subsequently, 829 mg of t-butyl α-{6(R)-[1(S)-t-butoxycarbonyl-5-phthalimidopentylamino]-5-oxo-2(S)-(2-thienyl)perhydro-1,4-thiazepin-4-yl}acetate were obtained as a foamy solid from the fractions next eluted.

$[α]^{23} + 30.1$ (c=1.0, dimethylformamide).

Nuclear Magnetic Resonance Spectrum (CDCl$_3$) δ ppm: 1.48 (18H, singlet); 1.2–1.9 (6H, multiplet); 2.5–4.8 (12H, multiplet); 6.9–7.3 (3H, multiplet); 7.6–8.0 (4H, multiplet).

EXAMPLE 2 t-Butyl α-{6(R)-[5-amino-1(S)-t-butoxycarbonylpentylamino]-5-oxo-2(S)-(2-thienyl)perhydro-1,4-thiazepin-4-yl}acetate 0.6 ml of hydrazine monohydrate was added to a solution of 815 mg of t-butyl α-{6(R)-[1(S)-t-butoxycarbonyl-5-phthalimidopentylamino]-5-oxo-2(S)-(2-thienyl)perhydro-1,4-thiazepin-4-yl}acetate (prepared as described in Example 1) dissolved in a mixture of 3 ml of methylene chloride and 3 ml of ethanol, whilst ice-cooling, and the mixture was stirred at room temperature for 4 days. At the end of this time, the precipitate which appeared in the reaction mixture was filtered off and the filtrate was concentrated by evaporation under reduced pressure. The residue was mixed with ethyl acetate and the precipitated material was filtered off. The ethyl acetate filtrate was dried over anhydrous magnesium sulfate and concentrated by evaporation under reduced pressure to remove the solvent. The residue was subjected to column chromatography through silica gel using mixtures of ethyl acetate and methanol in the proportions 10:1 and 4:1 by volume as the eluent to yield 302 mg of the title compound as syrup.

Nuclear Magnetic Resonance Spectrum (CDCl$_3$) δ ppm: 1.48 (18H, singlet); 1.2–1.9 (6H, multiplet); 2.5–4.8 (14H, multiplet); 6.9–7.35 (3H, multiplet).

EXAMPLE 3

α-{6(R)-[5-Amino-1(S)-carboxypentylamino]-5-oxo-2(S)-(2-thienyl)perhydro-1,4-thiazepin-4-yl}acetic acid dihydrochloride 302 mg of t-butyl α-{6(R)-[5-amino-1(S)-t-butoxycarbonylpentylamino]-5-oxo-2(S)-(2-thienyl)perhydro-1,4-thiazepin-4-yl}acetate (prepared as described in Example 2) were mixed with 3 ml of a 4N solution of hydrogen chloride in dioxane, and the mixture was stirred for 16 hours at room temperature. At the end of this time, the dioxane was distilled off under reduced pressure, and the residue was triturated with diethyl ether and filtered to yield 278 mg of the title compound as a powder.

$[α]^{23} + 73.3°$ (c=1.0, 1N aqueous hydrochloric acid).

Nuclear Magnetic Resonance Spectrum (CDCl$_3$) δ ppm: 1.3–2.2 (6H, multiplet); 2.4–5.2 (11H, multiplet); 6.95–7.6 (3H, multiplet).

EXAMPLE 4 t-Butyl α-[6(R)-(7-t-butoxycarbonylamino-1-ethoxycarbonylheptylamino)-5-oxo-2(S)-(2-thienyl)perhydro-1,4-thiazepin-4-yl]acetate.

1.5 g of t-butyl α-[6(R)-amino-5-oxo-2(S)-(2-thienyl)-perhydro-1,4-thiazepin-4-yl]acetate and 4.0 g of ethyl 2-bromo-8-t-butoxycarbonylaminooctanoate were dissolved in 20 ml of dimethylformamide, and 2.79 g of sodium carbonate were added to the mixture. The mixture was then stirred at 75° C. for 18 hours, after which ethyl acetate and water were added to it. The ethyl acetate layer was separated, washed with an aqueous solution of sodium chloride and dried over anhydrous magnesium sulfate. It was then concentrated by evaporation under reduced pressure, to remove the solvent. The residue was subjected to column chromatography through silica gel using a 4:1 by volume mixture of cyclohexane and ethyl acetate as the eluent.

442 mg of t-butyl α-{6(R)-[7-t-butoxycarbonylamino-1(R)-ethoxycarbonylheptylamino]-5-oxo-2-(S)-(2-thienyl)perhydro-1,4-thiazepin-4-yl}acetate were obtained from the fractions first eluted and isolated as a syrup.

$[α]^{23} + 46.3°$ (c=1.0, dimethylformamide).

Nuclear Magnetic Resonance Spectrum (CDCl$_3$) δ ppm: 1.25 (3H, triplet); 1.45 (9H, singlet); 1.48 (9H, singlet); 1.1–1.8 (10H, multiplet); 2.4–4.8 (15H, multiplet); 6.9–7.35 (3H, multiplet).

Subsequently, 525 mg of α-{6(R)-[7-t-butoxycarbonylamino-1(S)-ethoxycarbonylheptylamino]-5-oxo-2(S)-(2-thienyl)perhydro-1,4-thiazepin-4-yl}acetate was eluted and isolated as a syrup.

$[α]^{23} + 25.9°$ (c=1.0, dimethylformamide).

Nuclear Magnetic Resonance Spectrum (CDCl$_3$) δ ppm: 1.26 (3H, triplet, J=7 Hz); 1.43 (9H, singlet); 1.46 (9H, singlet); 1.1–1.8 (10H, multiplet); 2.4–4.75 (15H, multiplet); 6.9–7.35 (3H, multiplet).

EXAMPLE 5

α-{6(R)-[7-Amino-1(S)-ethoxycarbonylheptylamino]-5-oxo-2(S)-(2-thienyl)perhydro-1,4-thiazepin-4-yl}acetic acid dihydrochloride 510 mg of t-butyl α-{6(R)-[7-t-butoxycarbonylamino-1(S)-ethoxycarbonylheptylamino]-5-oxo-2(S)-(2-thienyl)perhydro-1,4-thiazepin-4-yl}acetate (prepared as described in Example 4) were dissolved in 5 ml of a 4N solution of hydrogen chloride in dioxane, and the mixture was allowed to stand for 18 hours. At the end of this time, the solvent was distilled off and the residue was triturated with diisopropyl ether and filtered to give 520 mg of a powder. This crude powder was purified by column chromatography through Diaion (trade mark) HP-20 using 20% and 40% v/v aqueous acetone (i.e. a mixture of either 20 or 40% acetone and correspondingly either 80 or 60% water) as the eluent. Concentration of the eluted fraction by evaporation under reduced pressure gave a foamy solid, which was dissolved in a 1 ml of a 4N solution of hydrogen chloride in dioxane. Evaporation of the dioxane under reduced pressure followed by trituration with diethyl ether and filtration gave 121 mg of the title compound.

$[\alpha]^{23} +63.7°$ (c=1.0, 1N aqueous hydrochloric acid).

Nuclear Magnetic Resonance Spectrum (hexadeuterated dimethyl sulfoxide) δ ppm: 1.1–2.1 (10H, multiplet); 1.26 (3H, triplet, J=7 Hz); 2.4–5.2 (13H, multiplet); 6.95–7.6 (3H, multiplet).

EXAMPLE 6

α-{6(R)-[7-Amino-1(S)-carboxyheptylamino]-5-oxo-2(S)-(2-thienyl)perhydro-1,4-thiazepin-4-yl}acetic acid 142 mg of α-{6(R)-[7-amino-1(S)-ethoxycarbonylheptylamino]-5-oxo-2(S)-(2-thienyl)perhydro-1,4-thiazepin-4-yl}acetic acid dihydrochloride (prepared as described in Example 5) were dissolved in 1.2 ml of a 1N aqueous solution of sodium hydroxide, and the mixture was allowed to stand for 24 hours. At the end of this time, the mixture as adjusted to a pH value of 4.8 by the addition of 1N aqueous hydrochloric acid and the resulted precipitates were collected by filtration to give 112 mg of the title compound.

$[\alpha]^{23} +93.9°$ (c=1, 1N aqueous hydrochloric acid).

Nuclear Magnetic Resonance Spectrum (CF$_3$CO$_2$D) δ ppm: 1.3–2.4 (10H, multiplet); 3.0–5.2 (11H, multiplet); 7.0–7.15 (3H, multiplet).

EXAMPLE 7 t-Butyl rel-α-[6(R)-(7-t-butoxycarbonylamino-1-ethoxycarbonylheptylamino)-5-oxo-2(R)-phenylperhydro-1,4-thiazepin-4-yl]acetate By following the same procedure as described in Example 4, a condensation reaction was carried out between 400 mg of t-butyl rel-α-[6(R)-amino-5-oxo-2(R)-phenylperhydro-1,4-thiazepin-4-yl]acetate and 1.08 g of ethyl 2-bromo-8-t-butoxycarbonylaminooctanoate in the presence of 0.76 g of sodium carbonate to give two diastereoisomers. These isomers were separated by column chromatography through silica gel, using a mixture of methylene chloride and ethyl acetate in the ratio 10:1 by volume as the eluent.

142 mg of the 1(R)-ethoxycarbonyl isomer were obtained as a syrup from the fractions eluted first.

Nuclear Magnetic Resonance Spectrum (CDCl$_3$) δ ppm: 1.25 (3H, triplet, J=7 Hz); 1.42 (9H, singlet); 1.45 (9H, singlet); 1.1–1.8 (10H, multiplet); 2.35–4.7 (15H, multiplet); 7.26 (5H, singlet).

144 mg of the 1(S)-ethoxycarbonyl isomer were obtained as a syrup from the fractions eluted next.

Nuclear Magnetic Resonance Spectrum (CDCl$_3$) δ ppm: 1.28 (3H, triplet, J=7 Hz); 1.42 (9H, singlet); 1.45 (9H, singlet); 1.1–1.8 (10H, multiplet); 2.4–4.7 (15H, multiplet); 7.28 (5H, singlet).

EXAMPLE 8 rel-α-{6(R)-[7-Amino-1(S)-ethoxycarbonylheptylamino]-5-oxo-2(R)-phenylperhydro-1,4-thiazepin-4-yl}acetic acid All 144 mg of the t-butyl rel-α-[6(R)-(7-t-butoxycarbonylheptylamino)-1(S)-ethoxycarbonylheptylamino-5-oxo-2(R)-phenylperhydro-1,4-thiazepin-4-yl]acetate isomer obtained from the second fraction to be eluted in the chromatography described in Example 7 were dissolved in a mixture of 1.5 ml of anisole and 2 ml of trifluoroacetic acid. The mixture was then stirred at room temperature for 4 hours. Concentration of the mixture by evaporation under reduced pressure afforded an oily residue, which was triturated with diisopropyl ether and filtered to give 143 mg of the crude title compound. The whole of this compound was dissolved in water containing 81 mg of sodium bicarbonate, adjusted to a pH value of 5.5 by the addition of 0.1N aqueous hydrochloric acid and purified by column chromatography through Diaion HP-20. Successive elution with 20% and 50% v/v aqueous methanol gave a fraction containing the title product, which was concentrated by evaporation under reduced pressure to give 69 mg of the title compound as a powder.

Nuclear Magnetic Resonance Spectrum (hexadeuterated dimethyl sulfoxide) δ ppm: 1.20 (3H, triplet, J=7 Hz); 1.1–1.7 (10H, multiplet); 2.4–4.5 (13H, multiplet); 7.36 (5H, singlet).

EXAMPLE 9 rel-α-{6(R)-[7-Amino-1(S)-carboxyheptylamino]-5-oxo-2(R)-phenylperhydro-1,4-thiazepin-4-yl}acetic acid 59.0 mg rel-α-{6(R)-[7-amino-1(S)-ethoxycarbonylheptylamino]-5-oxo-3(R)-phenylperhydro-1,4-thiazepin-4-yl]acetic acid (prepared as described in Example 8) were dissolved in 1.0 ml of a 0.5N aqueous solution of sodium hydroxide, and the mixture was stirred at room temperature for 3 hours. At the end of this time, the reaction mixture was adjusted to a pH value of 4.5 by the addition of 1N aqueous hydrochloric acid and was then concentrated by evaporation under reduced pressure to precipitate 45 mg of the title compound.

Nuclear Magnetic Resonance Spectrum (D$_2$O-DCl) δ ppm: 1.7–2.7 (10H, multiplet); 3.3–5.7 (11H, multiplet); 7.93 (5H, singlet).

EXAMPLE 10 t-Butyl rel-α-[6(R)-(1-ethoxycarbonyl-5-phthalimidopentylamino)-5-oxo-2(R)-phenylperhydro-1,4-thiazepin-4-yl]acetate By following the same procedure as described in Example 4, a condensation reaction was carried out between 336 mg of t-butyl rel-α-[6(R)-amino-5-oxo-2(R)-phenylperhydro-1,4-thiazepin-4-yl]acetate and 552 mg of ethyl 2-bromo-6-phthalimidohexanoate in the presence of 318 mg of sodium carbonate to give two diastereoisomers. These isomers were separated by column chromatography through silica gel using a mixture of cyclohexane and ethyl acetate in the ratio 5:1 by volume as the eluent.

206 mg of the 1(R)-ethoxycarbonyl isomer were obtained as a syrup from the fractions eluted first:

Nuclear Magnetic Resonance Spectrum (CDCl$_3$) δ ppm: 1.25 (3H, triplet, J=7 Hz); 1.47 (9H, singlet); 1.1–1.9 (6H, multiplet); 2.35–4.55 (14H, multiplet); 7.28 (5H, singlet); 7.5–8.0 (4H, multiplet).

230 mg of the 1(S)-ethoxycarbonyl isomer were obtained as a syrup from the fractions eluted next:

Nuclear Magnetic Resonance Spectrum (CDCl₃) δ ppm: 1.26 (3H, triplet, J=7 Hz); 1.47 (9H, singlet); 2.4–4.5 (14H, multiplet); 7.28 (5H singlet); 7.5–8.0 (4H, multiplet).

EXAMPLE 11 rel-α-{6(R)-[1(S)-Ethoxycarbonyl-5-phthalimidopentyl-amino]-5-oxo-2(R)-phenylperhydro-1,4-thiazepin-4-yl}acetic acid 206 mg of t-butyl rel-α-{6(R)-[1(S)-ethoxycarbonyl-5-phthalimidopentylamino)-5-oxo-2(R)-phenylperhydro-1,4-thiazepin-4-yl]acetate (prepared as described in Example 10) were dissolved in a mixture of 2 ml of anisole and 2 ml of trifluoroacetic acid. The mixture was stirred at room temperature for 4 hours, after which it was concentrated by evaporation under reduced pressure. The resulting gummy residue was triturated with diisopropyl ether and filtered to afford the trifluoroacetic acid salt of the title compound. This salt was suspended in a mixture of 4 ml of water containing 0.6 g of sodium bicarbonate and 4 ml of diisopropyl ether and adjusted to a pH value of 3 by the addition of 1N aqueous hydrochloric acid, whilst stirring, to precipitate 105 mg of the title compound.

Nuclear Magnetic Resonance Spectrum (CDCl₃) δ ppm: 1.26 (3H, triplet, J=7 Hz); 1.0–2.2 (6H, multiplet); 2.6–4.7 (13H, multiplet); 7.21 (5H, singlet); 7.5–7.9 (4H, multiplet).

EXAMPLE 12 t-Butyl α-[6(R)-(8-t-butoxycarbonylamino-1-ethoxycarbonyloctylamino)-5-oxo-2(S)-(2-thienyl)perhydro-1,4-thiazepin-4-yl]acetate.

1.3 g of t-butyl α-[6(R)-amino-5-oxo-2(S)-(2-thienyl)perhydro-1,4-thiazepin-4-yl]acetate was treated with 1.73 g of ethyl 2-bromo-9-t-butoxycarbonylaminononanoate prepared as described in Preparation 4) in a similar manner to that described in Example 4. The product was then subjected to column chromatography through silica gel using a mixture of benzene and ethyl acetate in the ratio 5:1 by volume as the eluent. 237 mg of t-butyl α-{6(R)-[8-t-butoxycarbonylamino-1(R)-ethoxycarbonyloctylamino]-5-oxo-2(S)-(2-thienyl)perhydro-1,4-thiazepin-4-yl}acetate was obtained as a syrup from the fractions eluted first.

$[\alpha]^{25}+43.3°$ (c=1, dimethylformamide).

Infrared Absorption Spectrum (liquid film) $v_{max}$ cm⁻¹: 3360, 1730, 1710, 1660.

Nuclear Magnetic Resonance Spectrum (CDCl₃) δ ppm: 1.26 (3H, triplet, J=7 Hz); 1.45 (9H, singlet); 1.48 (9H, singlet); 1.1–1.8 (12H, multiplet); 2.4–4.8 (11H, multiplet); 4.08 (2H, AB-quartet, Δδ=0.58 ppm, J=17 Hz); 4.16 (2H, quartet, J=7 Hz); 6.9–7.35 (3H, multiplet).

Subsequently, 283 mg of t-butyl α-{6(R)-[8-t-butoxycarbonylamino-1(S)-ethoxycarbonyloctylamino]-5-oxo-2(S)-(2-thienyl)perhydro-1,4-thiazepin-4-yl}acetate was obtained as a syrup from the fractions eluted next.

$[\alpha]^{25}+28.6°$ (c=1.0, dimethylformamide).

Infrared Absorption Spectrum (liquid film) $v_{max}$ cm⁻¹: 3360, 1730, 1705, 1655.

Nuclear Magnetic Resonance Spectrum (CDCl₃) δ ppm: 1.28 (3H, triplet); 1.44 (9H, singlet); 1.47 (9H, singlet); 1.1–1.8 (12H, multiplet); 2.4–4.75 (11H, multiplet); 4.08 (2H, AB-quartet, Δδ=0.50 ppm, J=17 Hz); 4.18 (2H, quartet, J=7 Hz); 6.9–7.35 (3H, multiplet).

EXAMPLE 13

α-{6(R)-[8-Amino-1(S)-ethoxycarbonyloctylamino]-5-oxo-2(S)-(2-thienyl)perhydro-1,4-thiazepin-4-yl}acetic acid dihydrochloride.

1.09 g of t-butyl α-{6(R)-[8-t-butoxycarbonylamino-1(S)-ethoxycarbonyloctylamino]-5-oxo-2(S)-(2-thienyl)perhydro-1,4-thiazepin-4-yl}acetate (prepared as described in Example 12) was treated in a similar manner to that described in Example 5 to give 0.78 g of the title compound as a powder.

$[\alpha]^{25}+61.1°$ (c=1, 1N aqueous hydrochloric acid).

Nuclear Magnetic Resonance Spectrum (hexadeuterated dimethyl sulfoxide) δ ppm: 1.1–2.1 (15H, multiplet); 2.5–5.1 (13H, multiplet); 6.95–7.55 (3H, multiplet).

EXAMPLE 14

α-{6(R)-[8-Amino-1(S)-carboxyoctylamino]-5-oxo-2(S)-(2-thienyl)perhydro-1,4-thiazepin-4-yl}acetic acid In a similar manner to that described in Example 6, treatment of 0.30 g of α-{6(R)-[8-amino-1(S)-ethoxycarbonyloctylamino]-5-oxo-2(S)-(2-thienyl)perhydro-1,4-thiazpin-4-yl}acetic acid dihydrochloride (prepared as described in Example 13) gave 0.13 g of the title compound as a powder, melting with coloration over 240° C.

$[\alpha]^{25}+96.1°$ (c=1.0, 1N aqueous hydrochloric acid).

Nuclear Magnetic Resonance Spectrum (CF₃CO₂D) δ ppm: 1.3–2.4 (12H, multiplet); 3.1–5.3 (11H, multiplet); 6.95–7.4 (3H, multiplet).

EXAMPLE 15 t-Butyl rel-α-[3(S)-(8-t-butoxycarbonylamino-1-ethoxycarbonyloctylamino)-2-oxo-6(R)-phenylperhydroazepin-1-yl]acetate 1.2 g of t-butyl rel-α-[3(S)-amino-2-oxo-6(R)-phenylperhydroazepin-1-yl]acetate was treated with 2.15 g of ethyl 2-bromo-9-t-butoxycarbonylaminononanoate prepared as described in Preparation 4) in a similar manner to that described in Example 4, to afford a reaction product, which was subjected to column chromatography through silica gel using a mixture of cyclohexane and ethyl acetate in the ratio of 1:1 by volume as the eluent.

Infrared Absorption Spectrum (liquid film) $v_{max}$ cm⁻¹: 3350, 1735, 1730, 1710, 1655.

Nuclear Magnetic Resonance Spectrum (CDCl₃) δ ppm: 1.27 (3H, triplet, J=7 Hz,); 1.47 (18H, singlet); 1.0–2.3 (16H, multiplet); 2.4–4.7 (9H, multiplet); 4.08 (2H, AB-quartet, Δδ=0.33 ppm, J=17 Hz); 4.18 (2H, quartet, J=7 Hz); 7.0–7.4 (5H, multiplet).

Subsequently, 0.68 g of t-butyl rel-α-{3(S)-[8-t-butoxycarbonylamino-1(S)-ethoxycarbonyloctylamino]-2-oxo-6(R)-phenylperhydroazepin-1-yl}acetate was eluted as a syrup.

Infrared Absorption Spectrum (liquid film) $v_{max}$ cm⁻¹: 3350, 1735, 1710, 1655.

Nuclear Magnetic Resonance Spectrum (CDCl₃) δ ppm: 1.27 (3H, triplet); 1.46 (18H, singlet); 1.1–2.2 (16H, multiplet); 2.8–4.7 (9H, multiplet); 4.07 (2H, AB-quartet, Δδ=0.33 ppm, J=17 Hz); 4.19 (2H, quartet, J=7 Hz, ); 7.05–7.45 (5H, multiplet).

EXAMPLE 16 rel-α-{3(S)-[8-Amino-1-(S)-ethoxycarbonyloctylamino]-2-oxo-6(R)-phenylperhydroazepin-1-yl}acetic acid dihydrochloride.

0.68 g of t-butyl rel-α-{3(S)-[8-t-butoxycarbonylamino-1(S)-ethoxycarbonyloctylamino]-2-oxo-6(R)-phenylperhydroazepin-1-yl}acetate (prepared as described in Example 15) was treated in the same manner as described in Example 5 to afford 0.45 g of the title compound as a powder.

Infrared Absorption Spectrum (Nujol) $\nu_{max}$ cm$^{-1}$: 2000–3780, 1750, 1730 (shoulder), 1660.

Nuclear Magnetic Resonance Spectrum (hexadeuterated dimethyl sulfoxide) δ ppm: 1.27 (3H, t, J=7 Hz, ) 1.1–2.2 (16H, multiplet); 2.6–4.7 (11H, multiplet); 7.35 (5H, broad singlet).

EXAMPLE 17 rel-α-{3(S)-[8-Amino-1(S)-carboxyoctylamino]-2-oxo6(R)-phenylperhydroazepin-1-yl}acetic acid.

In a similar manner to that described in Example 6, treatment of 0.30 g of rel-α-{3(S)-[8-amino-1(S)ethoxycarbonyloctylamino]-2-oxo-6(R)-phenylperhydroazepin-1-yl}acetic acid dihydrochloride (prepared as described in Example 16) gave an aqueous solution containing the title compound. This solution was subjected to column chromatography through porous resin HP-20 (Mitsubishi Kasei K.K.) eluted first with water and then with water containing 20% v/v of acetone. Concentration of the aqueous acetone fraction by evaporation under reduced pressure gave 0.16 g of the title compound as crystals, melting with coloration and softening over 205° C.

Infrared Absorption Spectrum (Nujol) $\nu_{max}$ cm$^{-1}$: 3330, 1670, 1590–1615.

Nuclear Magnetic Resonance Spectrum (D$_2$O+NaOD) δ ppm: 1.7–5.7 (multiplet); 4.50 (2H, AB-quartet, Δδ=0.44 ppm, J=17 Hz); 7.85 (5H, singlet).

EXAMPLE 18 t-Butyl α-{6(R)-[5-(1-t-butoxycarbonyl-4-piperidyl)1-ethoxycarbonylpentylamino]-5-oxo-2(S)-(2-thienyl)perhydro-1,4-thiazepin-4-yl}acetate A solution of 0.50 g of ethyl 6-(1-t-butoxycarbonyl-4-piperidy)-2-trifluoromethanesulfonyloxyhexanoate (prepared as described in Preparation 5) in 5ml of methylene chloride was added to a solution of 400 mg of t-butyl α-[6(R)-amino-5-oxo-2(S)-(2-thienyl)perhydro-1,4-thiazepin-4-yl]acetate and 0.2 ml of triethylamine in 5 ml of methylene chloride, and the solution was allowed to stand at room temperature overnight. The reaction mixture was then concentrated by evaporation under reduced pressure, and ethyl acetate and water were added to the residue. The ethyl acetate layer was separated, washed with water and dried over anhydrous magnesium sulfate. The solvent was removed by evaporation under reduced pressure, and the residue was subjected to silica gel column chromatography using a 10:1 by volume mixture of methylene chloride and ethyl acetate as the eluent.

261 mg of t-butyl α-{6(R)-[5-(1-t-butoxycarbonyl-4-piperidyl)-1(R)-ethoxycarbonylpentylamino]-5-oxo-2(S)-(2-thienyl)perhydro-1,4-thiazepin-4-yl}acetate were obtained as a syrupy substance from the fractions frist eluted.

$[\alpha]^{25}$ +27.0° (c=1.0, dimethylformamide).

Infrared Absorption Spectrum (liquid film) $\nu_{max}$ cm$^{-1}$: 3310, 1730, 1685, 1660.

Nuclear Magnetic Resonance Spectrum (CDCl$_3$) δ ppm: 0.9–1.9 (16H, multiplet); 1.48 (18H, singlet); 2.4–4.8 (11H, multiplet); 4.08 (2H, AB-quartet, Δδ=0.60 ppm, J=17 Hz); 4.17 (2H, quartet, J=7 Hz); 6.9–7.35 (3H, multiplet).

280 mg of t-butyl α-{6(R)-[5-(1-t-butoxycarbonyl-4-piperidyl)-1(S)-ethoxycarbonylpentylamino]5-oxo-2(S)-(2-thienyl)perhydro-1,4-thiazepin-4-yl}acetate were obtained as a syrupy substance from the fractions eluted next.

$[\alpha]^{25}$ +30.0° (c=1.0, dimethylformamide).

Infrared Absorption Spectrum (liquid film) $\nu_{max}$ cm$^{-1}$: 3300, 1730, 1682, 1660.

Nuclear Magnet Resonance Spectrum (CDCL$_3$) δ ppm: 0.9–1.9 (16H, multiplet); 1.48 (18H, singlet); 2.3–4.8 (11H, multiplet); 4.08 (2H, AB-quartet, Δδ=0.60 ppm, J=17 Hz); 4.19 (2H, quartet, J=7 Hz); 6.9–7.35 (3H, multiplet).

EXAMPLE 19

α-{6(R)-[1(S)-Ethoxycarbonyl-5-(4-piperidyl)-pentylamino]-5-oxo-2(S)-(2-thienyl)perhydro-1,4-thiazepin-4-yl}acetic acid dihydrochloride 2 ml of a 4N solution of hydrochloric acid in dioxane were added to 264 mg of t-butyl α-{6(R)[5-(1-t-butoxycarbonyl-4-piperidyl)-1(S)-ethoxycarbonylpentylamino]-5-oxo-2(S)-(2-thienyl)perhydro-1,4-thiazepin-4-yl}acetate (prepared as described in Example 18), and the mixture was allowed to stand at room temperature overnight. The solvent was then removed from the reaction mixture by evaporation under reduced pressure, and the residue was pulverized in diethyl ether and collected by filtration, to afford 208 mg of the title compound.

$[\alpha]^{25}$ +34.3° (c=1.0, dimethylformamide).

Infrared Absorption Spectrum (Nujol—trade mark—mull) $\nu_{max}$ cm$^{-1}$: 2000–3700, 1730, 1660.

Nuclear Magnetic Resonance Spectrum (hexadeuterated dimethyl sulfoxide) δ ppm: 0.9–2.1 and 2.4–5.1 (multiplets); 7.0–7.2 (2H, multiplet); 7.52 (1H, doublet, J=4 Hz).

EXAMPLE 20

α-{6(R)-[1(S)-Carboxy-5-(4-piperidy)pentylamino]-5-oxo-2(S)-(2-thienyl)perhydro-1,4-thiazepin-4-yl}acetic acid 1.54 ml of a 1N aqueous solution of sodium hydroxide was added to 150 mg of α-{6(R)-[1(S)-ethoxycarbonyl5-(4-piperidyl)pentylamino]-5-oxo-2(S)-(2-thienyl)perhydro-1,4-thiazepin-4-yl}acetic acid dihydrochloride (prepared as described in Example 19), and the mixture was stirred at room temperature for 17 hours. At the end of this time, the reaction mixture was adjusted to a pH value of 4.7 by adding 1N aqueous hydrochlodric acid, and the precipitate was collected by filtration, to give 95 mg of the title compound.

$[\alpha]^{25}$ +81.8° (c=1.0, 1N aqueous sodium hydroxide).

Infrared Absorption Spectrum (Nujol) $\nu_{max}$ cm$^{-1}$: 2000–3600, 1680, 1605.

Nuclear Magnetic Resonance Spectrum (D$_2$O+DCl) δ ppm: 1.7–2.7 (12H, multiplet); 3.2–5.8 (14H, multiplet); 7.5–7.75 (2H, multiplet); 7.95 (1H, doublet J=4 Hz).

EXAMPLE 21 t-Butyl rel-α-{3(S)-[5-(1-t-butoxycarbonyl-4piperidyl)-1-ethoxycarbonylpentylamino]-2-oxo-6(R)phenylperhydroazepin-1-yl}acetate 1.08 g of ethyl 2-bromo-6-(1-t-butoxycarbonyl4-piperidyl)hexanoate, 0.85 g of t-butyl rel-α-[3(S)amino-2-oxo-6(R)-phenylperhydroazepin-1-yl]acetate, 0.4 g of sodium iodide and 1.4 g of sodium carbonate were added to 15 ml of dimethylformamide, and the mixture was stirred at room temperature for 3 days. Ethyl acetate and water were then added to the reaction mixture, and, after stirring, the ethyl acetate layer was separated, washed with an aquous sodium chloride solution, and dried over anhydrous magnesium sulfate. The solvent was then removed by evaporation under reduced pressure, and the residue was subjected to silica gel column chromatography using a 2:1 by volume mixture of cyclohexane and ethyl acetate as the eluent.

574 mg of t-butyl rel-α-{3(S)-[5-(1-t-butoxycarbonyl-4-piperidyl)-1(R)-ethoxycarbonylpentylamino]-2-oxo-6(R)-phenylperhydroazepin-1-yl}acetate were obtained as a syrupy substance from the fraction first eluted.

Infrared Absorption Spectrum (liquid film) $\nu_{max}$ cm$^{-1}$: 3340, 1735, 1690, 1660.

Nuclear Magnetic Resonance Spectrum (CDCl) δ ppm: 0.9–2.2 (20H, multiplet); 1.47 (18H, singlet); 2.4–4.4 (9H, multiplet); 4.08 (2H, AB-quartet, Δδ=0.33 ppm, J=17 Hz); 4.17 (2H, quartet, J=7 Hz); 7.0–7.4 (5H, multiplet).

555 mg of t-butyl rel-α-{3(S)-[5-(1-t-butoxycarbonyl-4-piperidyl)-1(S)-ethoxycarbonylpentylamino]-2-oxo-6(R)-phenylperhydroazepin-1-yl}acetate were obtained as a syrupy substance from the fraction eluted next.

Infrared Absorption Spectrum (liquid film) $\nu_{max}$ cm$^{-1}$: 3330, 1760, 1690, 1600.

Nuclear Magnetic Resonance Spectrum (CDCl$_3$) δ ppm: 1.0–2.1 (20H, multiplet); 1.48 (18H, singlet); 2.4–4.2 (9H, multiplet); 4.05 (2H, AB-quartet, Δδ=0.36 ppm, J=17 Hz); 4.18 (2H, quartet, J=17 Hz); 7.05–7.45 (5H, multiplet).

EXAMPLE 22 rel-α-{3(S)-[1(S)-Ethoxycarbonyl-5-(4-piperidyl)pentylamino]-2-oxo-6(R)-phenylperhydroazepin-1-yl}acetic acid dihydrochloride 555 mg of t-butyl rel-α-{3(S)-[5-(1-t-butoxycarbonyl-4-piperidyl)-1(S)-ethoxycarbonylpentylamino]-2-oxo-6(R)-penylperhydrozaepin-1-yl}acetate (perpared as described in Example 21) were treated as described in Example 19, giving 423 mg of the title compound as a powdery substance.

Infrared Absorption Spectrum (Nujol) $\nu_{max}$ cm$^{-1}$: 2200–3200, 1750, 1715, 1660.

Nuclear Magnetic Resonance Spectrum (hexadeuterated dimethyl sulfoxide) δ ppm: 1.0–2.2 and 2.6–4.7 (multiplet); 7.30 (5H, broad singlet).

EXAMPLE 23 rel-α-{3(S)-[1(S)-Carboxy-5-(4-piperidyl)pentylamino]-2-oxo-6(R)-phenylperhydroazepin-1-yl}acetic acid A solution of 300 mg of rel-α-{3(S)-[1(S)ethoxycarbonyl-5-(4-piperidyl)pentylamino]-2-oxo-6(R)-phenylperhydroazepin-1-yl}acetic acid dihydrochloride (prepared as described in Example 22) in 3.2 ml of a 1N aqueous solution of sodium hydroxide was stirred for 16 hours at room temperature, and then its pH value was adjusted to a value of 4.5 by adding 1N aqueous hydrochloric acid. The resulting precipitate was collected by filtration and dissolved again in water containing a small amount of acetic acid. The resulting solution together with the filtrate was poured onto a column pached with a porous resin HP-20 (Mitsubishi Kasei Kogyo Co., Ltd.) and eluted first with water and then with 20% v/v aqueous acetone. The fractions first eluted with water contained sodium chloride and acetic acid, whilst the fractions eluted next with 20% v/v aqueous acetone contained the title compound. The latter fractions were concentrated by evaporation under reduced pressure to give 223 mg of the title compound as a powdery substance.

Infrared Absorption Spectrum (Nujol) $\nu_{max}$ cm$^{-1}$: 2000–3700, 1660, 1600–1610.

Nuclear Magnetic Resonance Spectrum (D$_2$O+DCl) δ ppm: 1.7–3.0 (16H, multiplet); 3.2–4.1 (6H, multiplet); 4.4–5.3 (6H, multiplet); 7.7–8.0 (5H, multiplet).

PREPARATION 1

Diethyl α-(6-cyanohexyl)malonate 2.3 g of sodium hydride (as a 55% w/w dispersion in mineral oil) were gradually added with ice cooling to a solution of 8.0 ml of diethyl malonate dissolved in 80 ml of dimethylformamide. The mixture was stirred for 30 minutes, and then 10 g of 7-bromoheptanenitrile were added dropwise to it over a period of 30 minutes. The mixture was then stirred at room temperature for 20 hours in an atmosphere of nitrogen. At the end of this time, ethyl acetate and water were added to the mixture, which was then acidified by adding an aqueous solution of potassium hydrogen sulfate, after which the organic layer was separated. This layer was dried over anhydrous magnesium sulfate and the solvent was removed by evaporation under reduced pressure. The residue was purified by column chromatography through silica gel (eluent: a 3:1 by volume mixture of cyclohexane and ethyl acetate) to afford 8.9 g of the title compound as a liquid.

Nuclear Magnetic Resonance Spectrum (CDCl$_3$) δ (ppm): 1.25 (6H, triplet, J=7 Hz); 1.2–2.1 (10H, multiplet); 2.2–2.5 (2H, multiplet); 3.31 (1H, doublet of doublets, J=5 & 6.5 Hz); 4.18 (4H, quartet, J=7 Hz).

Infrared Absorption Spectrum (liquid film) $\nu_{max}$ cm$^{-1}$: 2460, 1750 (shoulder) and 1730.

PREPARATION 2

Diethyl α-(7-t-butoxycarbonylaminoheptyl)malonate 8.9 g of diethyl α-(6-cyanohexyl)malonate (prepared as described in Preparation 1) were dissolved in 90 ml of ethanol, and the solution was stirred at 50° C. for 6 hours in the presence of Raney nickel and in an atmosphere of hydrogen. The catalyst was removed by filtration, and then 5.5 ml of triethylamine and 7.6 ml of di-t-butyl dicarbonate were added dropwise, in that order, whilst ice-cooling to the filtrate. The mixture was then stirred at room temperature for 1 hour, after which it was concentrated by evaporation under reduced pressure. The residue was dissolved in a 1:1 by volume mixture of ethyl acetate and cyclohexane and in water, after which the organic layer was separated. This organic layer was washed, in turn, with an aqueous solution of potassium hydrogen sulfate and with an aqueous solution of sodium bicarbonate and dried over anhydrous magnesium sulfate. The solvent was then removed by evaporation under reduced pressure. The residue was purified by column chromatography through silica gel (eluent: a 3:1 by volume mixture of cyclohexane and ethyl acetate), to afford 10.2 g of the title compound as a liquid.

Nuclear Magnetic Resonance Spectrum (CDCl$_3$) δ ppm: 1.25 (6H, triplet, J=7 Hz); 1.44 (9H, singlet); 1.2–2.1 (12H, multiplet); 2.9–3.45 (3H, multiplet); 4.19 (4H, quartet, J-7 Hz); 4.5 (1H, broad).

Infrared Absorption Spectrum (liquid film) $\nu_{max}$ cm$^{-1}$: 3400, 1750 (shoulder), 1730, 1715 (shoulder) and 1700 (shoulder).

PREPARATION 3

Diethyl α-bromo-α-(7-t-butoxycarbonylaminoheptyl)-malonate 1.2 g of sodium hydride (as a 55% w/w dispersion in mineral oil) were added at 5°–10° C. to a solution of 10.2 g of α-(7-t-butoxycarbonylaminoheptyl)malonate (prepared as described in Preparation 2) dissolved in 50 ml of dimethylformamide in an atmosphere of nitrogen. The mixture was then stirred for 30 minutes, after which 4.85 g of N-bromosuccinimide were added to it over a period of 20 minutes. The mixture was then stirred at room temperature for 15 minutes, after which ethyl acetate and water were added to it. The organic layer was separated and dried over anhydrous magnesium sulfate. The solvent was then removed by evaporation under reduced pressure. The residue was purified by column chromatography through silica gel (eluent: a 5:1 by volume mixture of cyclohexane and ethyl acetate), to afford 10.3 g of the title compound as a liquid.

Nuclear Magnetic Resonance Spectrum (CDCl$_3$) δ ppm: 1.28 (6H, triplet, J=7 Hz); 1.43 (9H, singlet); 1.2–1.6 (10H, multiplet); 2.0–2.4 (2H, multiplet); 2.9–3.3 (2H, multiplet); 4.25 (2H, quartet, J=7 Hz); 4.50 (1H, broad).

Infrared Absorption Spectrum (liquid film) $\nu_{max}$ cm$^{-1}$: 3430, 3360, 1740, 1710 and 1700 (shoulder).

PREPARATION 4

Ethyl 2-bromo-9-t-butoxycarbonylaminononanoate 10.3 g of diethyl α-bromo-α-(7-t-butoxycarbonylaminoheptyl)malonate (prepared as described in Preparation 3) were mixed with 60 ml of 8N aqueous hydrochloric acid, and the mixture was heated on an oil bath kept at 115° C. for 16 hours whilst stirring. The mixture was then concentrated by evaporation under reduced pressure, and water was separated as its benzene azeotrope. The residual yellow oily material (7.78 g) containing 9-amino-2-bromononanoic acid hydrochloride was dissolved in 100 ml of ethanol, and hydrogen chloride gas was bubbled through the solution for 2 hours whilst ice cooling. The mixture was then allowed to stand at room temperature for 16 hours. At the end of this time, the reaction mixture was concentrated by evaporation under reduced pressure, and the remaining hydrogen chloride in the residue was removed as its benzene azeotrope to afford 8.2 g of a brown liquid containing ethyl 9-amino-2-bromononanoate hydrochloride. This liquid was dissolved in 80 ml of methylene chloride. 10 ml of triethylamine and 6.3 ml of di-t-butyl dicarbonate were added dropwise to the solution, in that order. The mixture was then stirred at room temperature for 2 hours, after which the solvent was removed by evaporation under reduced pressure. The residue was dissolved in ethyl acetate and water. The solution was washed in turn with an aqueous solution of potassium hydrogen sulfate and with an aqueous solution of sodium bicarbonate, dried over anhydrous magnesium sulfate and concentrated by evaporation under reduced pressure to remove the solvent. The residue was purified by column chromatography through silica gel (eluent: a 5:1 by volume mixture of cyclohexane and ethyl acetate), to afford 6.35 g of the title compound as a liquid.

Nuclear Magnetic Resonance Spectrum (CDCl$_3$) δ ppm: 1.30 (3H, triplet, J=7 Hz); 1.46 (9H, singlet); 1.2–1.7 (10H, multiplet); 1.7–2.2 (2H, multiplet); 2.9–3.3 (2H, multiplet); 4.22 (2H, quartet, J=7 Hz); 4.1–4.4 (1H, multiplet); 4.55 (1H, broad).

Infrared Absorption Spectrum (liquid film) $\nu_{max}$ cm$^{-1}$: 3360, 1740 and 1700.

PREPARATION 5

Ethyl 6-(1-t-butoxycarbonyl-4-piperidyl)-2-trifluoromethanesulfonyloxyhexanoate 0.85 ml of pyridine and 0.56 ml of trifluoromethanesulfonic acid anhydride were added, in that order, to a solution of 1.0 g of ethyl 6-(1-t-butoxycarbonyl-4-piperidyl)-2-hydroxyhexanoate in 10 ml of anhydrous methylene chloride, whilst cooling on an ice-salt bath, and the mixture was then stirred for 30 minuites. At the end of this time, 20 ml of a 1:1 by volume mixture of cyclohexane and ethyl acetate were added to the reaction mixture, the solution was poured onto a short column packed with silica gel, and eluted with a 1:1 volume mixture of cyclohexane and ethyl acetate. The fraction containing the title compound was concentrated by evaporation under reduced pressure, to give 0.50 g of the title compound as a syrupy substance.

Nuclear Magnetic Resonance Spectrum (CDCl$_3$) δ ppm: 1.28 (3H, triplet, J=7 Hz); 1.44 (9H, singlet); 1.0–1.9 (13H, multiplet); 2.4–2.8 and 3.8–4.2 (4H, multiplet); 4.24 (2H, quartet, J=7 Hz); 5.15 (1H, triplet, J=6 Hz).

We claim:

1. A compound of formula (I)

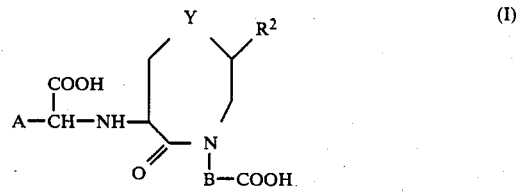

wherein:

A represents a group of formula (i):

or a group of formula (ii):

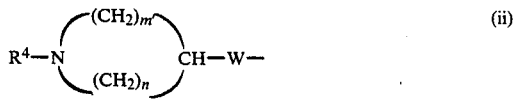

in which:

$R^4$ and $R^5$ are independently selected from the group consisting of hydrogen atoms, $C_1$–$C_6$ alkyl groups and amino-protecting groups selected from the group consisting of 2,2,2-trichloroethoxycarbonyl, 2-iodoethoxycarbonyl, trimethylsilylethoxycarbonyl, 2-(p-toluenesulfonyl)ethoxycarbonyl, t-butoxycarbonyl, allyloxycarbonyl, benzyloxycarbonyl, p-methoxybenzyloxycarbonyl, p-nitrobenzyloxycarbonyl, formyl, acetyl, benzoyl, chloroacetyl, trifluoroacetyl, methoxymethyl, benzyloxymethyl, benzyl, 3,4-dimethoxybenzyl, trityl, trimethylsilyl and t-butyldimethylsilyl groups;

Z represents a $C_1$-$C_8$ alkylene group;

W represents a $C_1$-$C_6$ alkylene group or a group of formula $-(CH_2)_k-X-(CH_2)_l-$, wherein X represents an oxygen or sulfur atom, k represents the cypher 0 or an integer from 1 to 5 and l represents an integer from 1 to 5; and m and n are the same or different and each represents an integer from 1 to 6;

$R^2$ represents a $C_1$-$C_6$ alkyl group, a $C_3$-$C_8$ cycloalkyl group, a $C_6$-$C_{10}$ carbocyclic aryl group or a heterocyclic group selected from the group consisting of isooxazolyl, 1,3,4-oxadiazolyl, 1,3,4-thiadiazolyl groups and said isooxazolyl, 1,3,4-oxadiazolyl and 1,3,4-thiadizolyl groups which are substituted with at least one $C_1$-$C_4$ alkyl substituent, said aryl groups being unsubstituted or having at least one substituent selected from the group consisting of substituents (a), defined below;

B represents a $C_1$-$C_2$ alkylene group;

Y represents a sulfur atom or a methylene group; and substituents (a):

$C_1$-$C_6$ alkyl groups, aralkyl groups wherein the alkyl part is $C_1$-$C_6$ alkyl and the aryl part is $C_6$-$C_{10}$ carbocyclic aryl which has from 0 to 3 substituents selected from the group consisting of substituents (a) which are not aryl groups, hydroxy groups, $C_1$-$C_6$ alkoxy groups, $C_6$-$C_{10}$ carbocyclic aryl groups having from 0 to 3 substituents selected from the group consisting of substituents (a) which are not aryl groups, aralkyloxy groups where the alkyl part is $C_1$-$C_6$ alkyl and the aryl part is $C_6$-$C_{10}$ carbocyclic aryl which has from 0 to 3 substituents selected from the group consisting of substituents (a) which are not aryl groups, $C_6$-$C_{10}$ aryloxy groups, halogen atoms, nitro groups, cyano groups, carboxy groups, alkoxycarbonyl groups having a total of from 2 to 7 carbon atoms, amino groups, $C_1$-$C_6$ alkylamino groups, dialkylamino groups wherein each alkyl part is $C_1$-$C_6$ alkyl, carbamoyl groups, alkylcarbamoyl groups where the alkyl part is $C_1$-$C_6$ alkyl, dialkylcarbamoyl groups where each alkyl part is $C_1$-$C_6$ alkyl, mercapto groups, $C_1$-$C_6$ alkylthio groups, $C_6$-$C_{10}$ carbocyclic arylthio groups, $C_1$-$C_6$ alkylsulfonyl groups and $C_6$-$C_{10}$ carbocyclic arylsulfonyl groups wherein the aryl part has from 0 to 3 $C_1$-$C_6$ alkyl substituents; and pharmaceutically acceptable salts and esters thereof.

2. A compound as claimed in claim 1, having the formula (Ia):

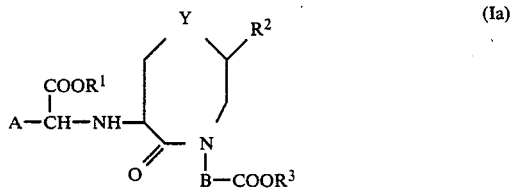

wherein A, B, Y and $R^2$ are as defined in claim 1 and $R^1$ and $R^3$ are independently selected from the group consisting of hydrogen atoms, $C_1$-$C_{10}$ alkyl groups, aralkyl groups in which the aryl part is a $C_6$-$C_{10}$ carbocyclic aryl group and the alkyl part is $C_1$-$C_6$ alkyl, $C_6$-$C_{14}$ carbocyclic aryl groups, phthalidyl groups and trialkylsilyl groups where each alkyl part is $C_1$-$C_6$ alkyl, said aralkyl, aryl and phthalidyl groups represented by $R^1$ and $R^3$ being unsubstituted or having at least one substituent selected from the group consisting of substituents (a), defined in claim 1.

3. A compound of formula (I) as claimed in claim 1, wherein:

A represents a group of formula (i):

or a group of formula (ii):

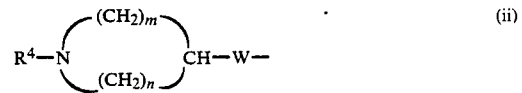

in which:

$R^4$ and $R^5$ both represent hydrogen atoms;

Z represents a $C_4$-$C_8$ alkylene group;

W represents a $C_2$-$C_4$ alkylene group or a group of formula $-(CH_2)_k-S-(CH_2)_l-$, wherein k represents the cypher 0 or the integer 1 or 2 and l represents an integer from 1 to 3; and m and n are the same or different and each represents the integer 1 or 2;

$R^2$ represents a phenyl group, a naphthyl group or one of the substituted or unsubstituted heterocyclic groups defined in claim 1, said phenyl and naphthyl groups being unsubstituted or having at least one substituent selected from the group consisting of substituents (a), defined in claim 1;

B represents a methylene group; and

Y represents a sulfur atom or a methylene group; and pharmaceutically acceptable salts thereof.

4. A compound of formula (I) as claimed in claim 1, wherein:

A represents a group of formula (i):

or a group of formula (ii):

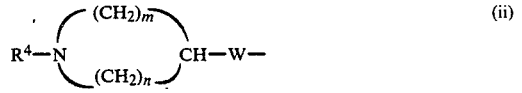

in which:

$R^4$ and $R^5$ both represent hydrogen atoms;

Z represents a $C_7$ or $C_8$ alkylene group;

W represents a $C_3$ or $C_4$ alkylene group or a group of formula $-(CH_2)_k-S-(CH_2)_l-$, wherein k represents the cypher 0 or the integer 1 and l represents an integer from 1 to 3;

m represents the integer 1 or 2; and n represents the integer 2;

$R^2$ represents a phenyl group, a thienyl group, a furyl group, an oxazolyl group, an isoxazolyl group, a thiazolyl group or a 1,3,4-thiadiazolyl group;

B represents a methylene group; and

Y represents a sulfur atom or a methylene group;

and pharmaceutically acceptable salts thereof.

5. A compound of formula (I) as claimed in claim 1, wherein:
A represents a group of formula H$_2$N—Z—, in which Z represents a C$_7$ or C$_8$ alkylene group;
R$^2$ represents a phenyl group, a 2-thienyl group, a 3-thienyl group or a 2-furyl group;
B represents a methylene group; and
Y represents a sulfur atom or a methylene group;
and pharmaceutically acceptable salts thereof.

6. A compound of formula (I) as claimed in claim 1, wherein:
A represents a group of formula H$_2$N—Z—, in which Z represents a C$_7$ or C$_8$ alkylene group;
R$^2$ represents a 2-thienyl group, a 3-thienyl group or a 2-furyl group;
B represents a methylene group; and
Y represents a sulfur atom;
and pharmaceutically acceptable salts thereof.

7. A compound of formula (I) as claimed in claim 1, wherein:
A represents a group of formula (iia):

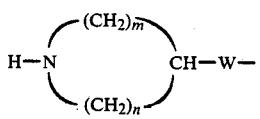

in which:
W represents a tetramethylene group or a group of formula —(CH$_2$)$_k$—S—(CH$_2$)$_l$—, wherein k represents the cypher 0 or the integer 1 and l represents an integer from 1 to 3;
m represents the integer 2; and
n represents the integer 2;
R$^2$ represents a phenyl group, a 2-thienyl group, a 3-thienyl group or a 2-furyl group;
B represents a methylene group; and
Y represents a sulfur atom or a methylene group;
and pharmaceutically acceptable salts thereof.

8. A compound of formula (I) as claimed in claim 1, wherein:
A represents a group of formula (iia):

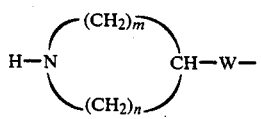

in which:
W represents a tetramethylene group or a group of formula —(CH$_2$)$_k$—S—(CH$_2$)$_l$—, wherein k represents the cypher 0 or the integer 1 and l represents an integer from 1 to 3;
m represents the integer 2; and
n represents the integer 2;
R$^2$ represents a 2-thienyl group, a 3-thienyl group or a 2-furyl group;
B represents a methylene group; and
Y represents a sulfur atom;
and pharmaceutically acceptable salts thereof.

9. A compound as claimed in claim 1, selected from the group consisting of α-[6-(8-amino-1-carboxyoctylamino)-5-oxo-2-(2-thienyl)perhydro-1,4-thiazepin-4-yl]acetic acid and pharmaceutically acceptable salts thereof.

10. A compound as claimed in claim 1, selected from the group consisting of α-[6-(9-amino-1-carboxynonylamino)-5-oxo-2-(2-thienyl)perhydro-1,4-thiazepin-4-yl]acetic acid and pharmaceutically acceptable salts thereof.

11. A compound as claimed in claim 1, selected from the group consisting of α-[6-(8-amino-1-carboxyoctylamino)-5-oxo-2-(3-thienyl)perhydro-1,4-thiazepin-4-yl]acetic acid and pharmaceutically acceptable salts thereof.

12. A compound as claimed in claim 1, selected from the group consisting of α-[6-(8-amino-1-carboxyoctylamino)-5-oxo-2-(2-furyl)perhydro-1,4-thiazepin-4-yl]acetic acid and pharmaceutically acceptable salts thereof.

13. A compound as claimed in claim 1, selected from the group consisting of α-[6-(8-amino-1-carboxyoctylamino)-5-oxo-2-phenylperhydro-1,4-thiazepin-4-yl]acetic acid and pharmaceutically acceptable salts thereof.

14. A compound as claimed in claim 1, selected from the group consisting of α-[3-(8-amino-1-carboxyoctylamino)-2-oxo-6-(2-thienyl)perhydroazepin-1-yl]acetic acid and pharmaceutically acceptable salts thereof.

15. A compound as claimed in claim 1, selected from the group consisting of α-[3-(9-amino-1-carboxynonylamino)-2-oxo-6-(2-thienyl)perhydroazepin-1-yl]acetic acid and pharmaceutically acceptable salts thereof.

16. A compound as claimed in claim 1, selected from the group consisting of α-[3-(8-amino-1-carboxyoctylamino)-2-oxo-6-phenylperhydroazepin-1-yl]acetic acid and pharmaceutically acceptable salts thereof.

17. A compound as claimed in claim 1, selected from the group consisting of α-[3-(9-amino-1-carboxynonylamino)-2-oxo-6-phenylperhydroazepin-1-yl]acetic acid and pharmaceutically acceptable salts thereof.

18. A compound as claimed in claim claim 1, selected from the group consisting of α-(6-[1-carboxy-5-(4-piperidyl)pentylamino]-5-oxo-2-(2-thienyl)perhydro-1,4-thiazepin-4-yl)acetic acid and pharmaceutically acceptable salts thereof.

19. A compound as claimed in claim 1, selected from the group consisting of α-(6-[1-carboxy-5-(4-piperidyl)pentylamino]-5-oxo-2-phenylperhydro-1,4-thiazepin-4-yl]acetic acid and pharmaceutically acceptable salts thereof.

20. A compound as claimed in claim 1, selected from the group consisting of α-(6-[1-carboxy-5-(4-piperidyl)pentylamino]-5-oxo-2-(3-thienyl)perhydro-1,4-thiazepin-4-yl]acetic acid and pharmaceutically acceptable salts thereof.

21. A compound as claimed in claim 1, selected from the group consisting of α-(6-[1-carboxy-5-(4-piperidyl)pentylamino]-5-oxo-2-(2-furyl)perhydro-1,4-thiazepin-4-yl]acetic acid and pharmaceutically acceptable salts thereof.

22. A compound as claimed in claim 1, selected from the group consisting of α-(3-[1-carboxy-5-(4-piperidyl)pentylamino]-2-oxo-6-(2-thienyl)perhydroazepin-1-yl)acetic acid and pharmaceutically acceptable salts thereof.

23. A compound as claimed in claim 1, selected from the group consisting of α-(3-[1-carboxy-5-(4-piperidyl)pentylamino]-2-oxo-6-(3-thienyl)perhydroazepin-1- yl)acetic acid and pharmaceutically acceptable salts thereof.

24. A compound as claimed in claim 1, selected from the group consisting of α-(3-[1-carboxy-5-(4-piperidyl)-pentylamino]-2-oxo-6-phenylperhydroazepin-1-yl)acetic acid and pharmaceutically acceptable salts thereof.

25. A compound as claimed in claim 1, selected from the group consisting of α-(6(R)-[8-amino-1(S)-carboxyoctylamino]-5-oxo-2(S)-(2-thienyl)perhydro-1,4-thiazepin-4-yl)acetic acid and pharmaceutically acceptable salts thereof.

26. A compound as claimed in claim 1, selected from the group consisting of α-(3(S)-[8-amino-1(S)-carboxyoctylamino]-2-oxo-6(R)-phenylperhydroazepin-1-yl)acetic acid and pharmaceutically acceptable salts thereof.

27. A compound as claimed in claim 1, selected from the group consisting of α-(6(R)-[1(S)-carboxy-5-(4-piperidyl)pentylamino]-5-oxo-2(S)-(2-thienyl)perhydro-1,4-thiazepin-4-yl)acetic acid and pharmaceutically acceptable salts thereof.

28. A compound as claimed in claim 1, selected from the group consisting of α-(3(S)-[1(S)-carboxy-5-(4-piperidyl)pentylamino]-2-oxo-6(R)-phenylperhydroazepin-1-yl)acetic acid and pharmaceutically acceptable salts thereof.

29. A pharmaceutical composition for the treatment of angiotensin-induced hypertension, which composition comprises an effective amount of a hypotensive agent in admixture with a pharmaceutically acceptable carrier or diluent, wherein said hypotensive agent is selected from the group consisting of compounds of formula (I):

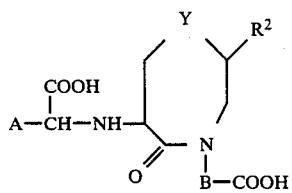

wherein:
A represents a group of formula (i):

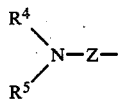

or a group of formula (ii):

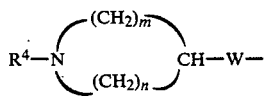

in which:
$R^4$ and $R^5$ are independently selected from the group consisting of hydrogen atoms, $C_1$-$C_6$ alkyl groups and amino-protecting groups selected from the group consisting of 2,2,2-trichloroethoxycarbonyl, 2-iodoethoxycarbonyl, trimethylsilylethoxycarbonyl, 2-(p-toluenesulfonyl)ethoxycarbonyl, t-butoxycarbonyl, allyloxycarbonyl, benzyloxycarbonyl, p-methoxybenzyloxycarbonyl, p-nitrobenzyloxycarbonyl, formyl, acetyl, benzoyl, chloroacetyl, trifluoroacetyl, methoxymethyl, benzyloxymethyl, benzyl, 3,4-dimethoxybenzyl, trityl, trimethylsilyl and t-butyldimethylsilyl groups;

Z represents a $C_1$-$C_8$ alkylene group;

W represents a $C_1$-$C_6$ alkylene group or a group of formula —$(CH_2)_k$—X—$(CH_2)_l$—, wherein X represents an oxygen or sulfur atom, k represents the cypher O or an integer from 1 to 5 and l represents an integer from 1 to 5; and m and n are the same or different and each represents an integer from 1 to 6;

$R^2$ represents a $C_1$-$C_6$ alkyl group, a $C_3$-$C_8$ cycloalkyl group, a $C_6$-$C_{10}$ carbocyclic aryl group or a heterocyclic group selected from the group consisting of isooxazolyl, 1,3,4-oxadiazolyl, 1,3,4-thiadiazolyl groups and said isooxazolyl, 1,3,4-oxadiazolyl and 1,3,4-thiadizolyl groups which are substituted with at least one $C_1$-$C_4$ alkyl substituent, said aryl groups being unsubstituted or having at least one substituent selected from the group consisting of substituents (a), defined below;

B represents a $C_1$-$C_2$ alkylene group;

Y represents a sulfur atom or a methylene group; and substituents (a):

$C_1$-$C_6$ alkyl groups, aralkyl groups wherein the alkyl part is $C_1$-$C_6$ alkyl and the aryl part is $C_6$-$C_{10}$ carbocyclic aryl which has from 0 to 3 substituents selected from the group consisting of substituents (a) which are not aryl groups, hydroxy groups, $C_1$-$C_6$ alkoxy groups, $C_6$-$C_{10}$ carbocyclic aryl groups having from 0 to 3 substituents selected from the group consisting of substituents (a) which are not aryl groups, aralkyloxy groups where the alkyl part is $C_1$-$C_6$ alkyl and the aryl part is $C_6$-$C_{10}$ carbocyclic aryl which has from 0 to 3 substituents selected from the group consisting of substituents (a) which are not aryl groups, $C_6$-$C_{10}$ aryloxy groups, halogen atoms, nitro groups, cyano groups, carboxy groups, alkoxycarbonyl groups having a total of from 2 to 7 carbon atoms, amino groups, $C_1$-$C_6$ alkylamino groups, dialkylamino groups wherein each alkyl part is $C_1$-$C_6$ alkyl, carbamoyl groups, alkylcarbamoyl groups where the alkyl part is $C_1$-$C_6$ alkyl, dialkylcarbamoyl groups where each alkyl part is $C_1$-$C_6$ alkyl, mercapto groups, $C_1$-$C_6$ alkylthio groups, $C_6$-$C_{10}$ carbocyclic arylthio groups, $C_1$-$C_6$ alkylsulfonyl groups and $C_6$-$C_{10}$ carbocyclic arylsulfonyl groups wherein the aryl part has from 0 to 3 $C_1$-$C_6$ alkyl substituents;

and pharmaceutically acceptable salts and esters thereof.

30. A composition as claimed in claim 29, wherein said antihypotensive agent is a compound of formula (I) in which:

A represents a group of formula (i):

or a group of formula (ii):

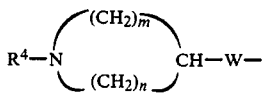

in which:
R[4] and R[5] both represent hydrogen atoms;
Z represents a $C_4$-$C_8$ alkylene group;
W represents a $C_2$-$C_4$ alkylene group or a group of formula $-(CH_2)_k-S-(CH_2)_l-$, wherein k represents the cypher O or the integer 1 or 2 and l represents an integer from 1 to 3; and
m and n are the same or different and each represents the integer 1 or 2;
R[2] represents a phenyl group, a naphthyl group or one of the substituted or unsubstituted heterocyclic groups defined in claim 29, said phenyl and naphthyl groups being unsubstituted or having at least one substituent selected from the group consisting of substituents (a), defined in claim 29;
B represents a methylene group; and
Y represents a sulfur atom or a methylene group;
or a pharmaceutically acceptable salt thereof.

31. A composition as claimed in claim 29, wherein said antihypotensive agent is a compound of formula (I) in which:
A represents a group of formula (i):

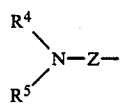

or a group of formula (ii):

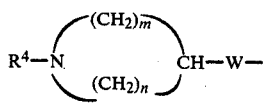

in which:
R[4] and R[5] both represent hydrogen atoms;
Z represents a $C_7$ or $C_8$ alkylene group;
W represents a $C_3$ or $C_4$ alkylene group or a group of formula $-(CH_2)_k-S-(CH_2)_l-$, wherein k represents the cypher O or the integer 1 and l represents an integer from 1 to 3;
m represents the integer 1 or 2; and
n represents the integer 2;
R[2] represents a phenyl group, a thienyl group, a furyl group, an oxazolyl group, an isoxazolyl group, a thiazolyl group or a 1,3,4-thiadiazolyl group;
B represents a methylene group; and
Y represents a sulfur atom or a methylene group;
or a pharmaceutically acceptable salt thereof.

32. A composition as claimed in claim 29, wherein said antihypotensive agent is a compound of formula (I) in which:
A represents a group of formula $H_2N-Z-$, in which Z represents a $C_7$ or $C_8$ alkylene group;
R[2] represents a phenyl group, a 2-thienyl group, a 3-thienyl group or a 2-furyl group;
B represents a methylene group; and
Y represents a sulfur atom or a methylene group;
or a pharmaceutically acceptable salt thereof.

33. A composition as claimed in claim 29, wherein said antihyoptensive agent is a compound of formula (I) in which:
A represents a group of formula $H_2N-Z-$, in which Z represents a $C_7$ or $C_8$ alkylene group;
R[2] represents a 2-thienyl group, a 3-thienyl group or a 2-furyl group;
B represents a methylene group; and
Y represents a sulfur atom;
or a pharmaceutically acceptable salt thereof.

34. A composition as claimed in claim 29, wherein said antihypotensive agent is a compound of formula (I) in which:
A represents a group of formula (iia):

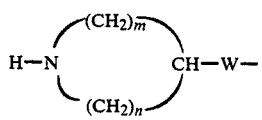

in which:
W represents a tetramethylene group or a group of formula $-(CH_2)_k-S-(CH_2)_l-$, wherein k represents the cypher 0 or the integer 1 and l represents an integer from 1 to 3;
m represents the integer 2; and
n represents the integer 2;
R[2] represents a phenyl group, a 2-thienyl group, a 3-thienyl group or a 2-furyl group;
B represents a methylene group; and
Y represents a sulfur atom or a methylene group;
or a pharmaceutically acceptable salt thereof.

35. A composition as claimed in claim 29, wherein said antihyoptensive agent is a compound of formula (I) in which:
A represents a group of formula (iia):

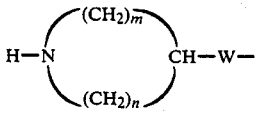

in which:
W represents a tetramethylene group or a group of formula $-(CH_2)_k-S-(CH_2)_l-$, wherein k represents the cypher 0 or the integer 1 and l represents an integer from 1 to 3;
m represents the integer 2; and
n represents the integer 2;
R[2] represents a 2-thienyl group, a 3-thienyl group or a 2-furyl group;
B represents a methylene group; and
Y represents a sulfur atom;
or a pharmaceutically acceptable salt thereof.

36. A composition as claimed in claim 29, wherein said hypotensive agent is selected from the group consisting of:
α-[6-(8-amino-1-carboxyoctylamino)-5-oxo-2-(2-thienyl)perhydro-1,4-thiazepin-4-yl]acetic acid;
α-[6-(9-amino-1-carboxynonylamino)-5-oxo-2-(2-thienyl)perhydro-1,4-thiazepin-4-yl]acetic acid;
α-[6-(8-amino-1-carboxyoctylamino)-5-oxo-2-(3-thienyl)perhydro-1,4-thiazepin-4-yl]acetic acid;
α-[6-(8-amino-1-carboxyoctylamino)-5-oxo-2-(2-furyl)perhydro-1,4-thiazepin-4-yl]acetic acid;

α-[6-(8-amino-1-carboxyoctylamino)-5-oxo-2-phenyl-perhydro-1,4-thiazepin-4-yl]acetic acid;
α-[3-(8-amino-1-carboxyoctylamino)-2-oxo-6-(2-thienyl)perhydroazepin-1-yl]acetic acid;
α-[3-(9-amino-1-carboxynonylamino)-2-oxo-6-(2-thienyl)perhydroazepin-1-yl]acetic acid;
α-[3-(8-amino-1-carboxyoctylamino)-2-oxo-6-phenyl-perhydroazepin-1-yl]acetic acid;
α-[3-(9-amino-1-carboxynonylamino)-2-oxo-6-phenylperhydroazepin-1-yl]acetic acid;
α-{6-[1-carboxy-5-(4-piperidyl)pentylamino]-5-oxo-2-(2-thienyl)perhydro-1,4-thiazepin-4-yl}acetic acid;
α-{6-[1-carboxy-5-(4-piperdiyl)pentylamino]-5-oxo-2-phenylperhydro-1,4-thiazepin-4-yl]acetic acid;
α-{6-[1-carboxy-5-(4-piperidyl)pentylamino]-5-oxo-2-(3-thienyl)perhydro-1,4-thiazepin-4-yl]acetic acid;
α-{6-[1-carboxy-5-(4-piperidyl)pentylamino]-5-oxo-2-(2-furyl)perhydro-1,4-thiazepin-4-yl]acetic acid;
α-{3-[1-carboxy-5-(4-piperidyl)pentylamino]-2-oxo-6-(2-thienyl)perhydroazepin-1-yl)acetic acid;
α-{3-[1-carboxy-5-(4-piperidyl)pentylamino]-2-oxo-6-(3-thienyl)perhydroazepin-1-yl)acetic acid;
α-{3-[1-carboxy-5-(4-piperidyl)pentylamino]-2-oxo-6-phenylperhydroazepin-1-yl)acetic acid;
and pharmaceutically acceptable salts thereof.

37. A method of treating angiostensin-induced hypertension in a mammal, by administering to said mammal an effective amount of a hypotensive agent, wherein said hypotensive agent is selected from the group consisting of compounds of formula (I):

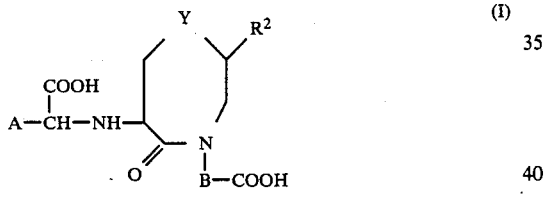

wherein:
A represents a group of formula (i):

or a group of formula (ii):

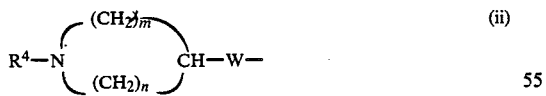

in which:
$R^4$ and $R^5$ are independently selected from the group consisting of hydrogen atoms, $C_1$-$C_6$ alkyl groups and amino-protecting groups selected from the group consisting of 2,2,2-trichloroethoxycarbonyl, 2-iodoethoxycarbonyl, trimethylsilyethoxycarbonyl, 2-(p-toluenesulfonyl)ethoxycarbonyl, t-butyoxycarbonyl, allyloxycarbonyl, benzyloxycarbonyl, p-methoxybenzyloxycarbonyl, p-nitrobenzyloxycarbonyl, formyl, acetyl, benzoyl, chloroacetyl, trifluoroacetyl, methoxymethyl, benzyloxymethyl, benzyl, 3,4-dimethoxybenzyl, trityl, trimethylsilyl and t-butyldimethylsilyl groups;

Z represents a $C_1$-$C_8$ alkylene group;

W represents a $C_1$-$C_6$ alkylene group or a group of formula —$(CH_2)_k$—X—$(CH_2)_l$—, wherein X represents an oxygen or sulfur atom, k represents the cypher 0 or an integer from 1 to 5 and l represents an integer from 1 to 5; and m and n are the same or different and each represents an integer from 1 to 6;

$R^2$ represents a $C_1$-$C_6$ alkyl group, a $C_3$-$C_8$ cycloalkyl group, a $C_6$-$C_{10}$ carbocyclic aryl group or a heterocyclic group selected from the group consisting of isooxazolyl, 1,3,4-oxadiazolyl, 1,3,4-thiadiazolyl groups and said isooxazolyl, 1,3,4-oxadiazolyl and 1,3,4-thiadiazolyl groups which are substituted with at least one $C_1$-$C_4$ alkyl substituent, said aryl groups being unsubstituted or having at least one substituent selected from the group consisting of substituents (a), defined below;

B represents a $C_1$-$C_2$ alkylene group;

Y represents a sulfur atom or a methylene group; and substituents (a):

$C_1$-$C_6$ alkyl groups, aralkyl groups wherein the alkyl part is $C_1$-$C_6$ alkyl and the aryl part is $C_6$-$C_{10}$ carbocyclic aryl which has from 0 to 3 substituents selected from the group consisting of substituents (a) which are not aryl groups, hydroxy groups, $C_1$-$C_6$ alkoxy groups, $C_6$-$C_{10}$ carbocyclic aryl groups having from 0 to 3 substituents selected from the group consisting of substituents (a) which are not aryl groups, aralkyloxy groups where the alkyl part is $C_1$-$C_6$ alkyl and the aryl part is $C_6$-$C_{10}$ carbocyclic aryl which has from 0 to 3 substituents selected from the group consisting of substituents (a) which are not aryl groups, $C_6$-$C_{10}$ aryloxy groups, halogen atoms, nitro groups, cyano groups, carboxy groups, alkoxycarbonyl groups having a total of from 2 to 7 carbon atoms, amino groups, $C_1$-$C_6$ alkylamino groups, dialkylamino groups wherein each alkyl part is $C_1$-$C_6$ alkyl, carbamoyl groups, alkylcarbamoyl groups where the alkyl part is $C_1$-$C_6$ alkyl, dialkylcarbamoyl groups where each alkyl part is $C_1$-$C_6$ alkyl, mercapto groups, $C_1$-$C_6$ alkylthio groups, $C_6$-$C_{10}$ carbocyclic arylthio groups, $C_1$-$C_6$ alkylsulfonyl groups and $C_6$-$C_{10}$ carbocyclic arylsulfonyl groups wherein the aryl part has from 0 to 3 $C_1$-$C_6$ alkyl substituents;

and pharmaceutically acceptable salts and esters thereof.

38. A method as claimed in claim 37, wherein said antihypotensive agent is a compound of formula (I) in which:

A represents a group of formula (i):

or a group of formula (ii):

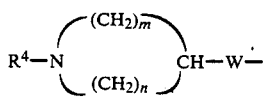

in which:
R[4] and R[5] both represent hydrogen atoms;
Z represents a C$_4$-C$_8$ alkylene group;
W represents a C$_2$-C$_4$ alkylene group or a group of formula —(CH$_2$)$_k$—S—(CH$_2$)$_l$—, wherein k represents the cypher 0 or the integer 1 or 2 and l represents an integer from 1 to 3; and
m and n are the same or different and each represents the integer 1 or 2;
R[2] represents a phenyl group, a naphthyl group or one of the substituted or unsubstituted heterocyclic groups defined in claim 37, said phenyl and naphthyl groups being unsubstituted or having at least one substituent selected from the group consisting of substituents (a), defined in claim 37;
B represents a methylene group; and
Y represents a sulfur atom or a methylene group;
or a pharmaceutically acceptable salt thereof.

39. A method as claimed in claim 37, wherein said antihypotensive agent is a compound of formula (I) in which:
A represents a group of formula (i):

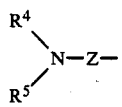

or a group of formula (ii):

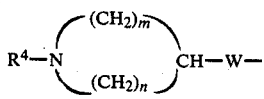

in which:
R[4] and R[5] both represent hydrogen atoms;
Z represents a C$_7$ or C$_8$ alkylene group;
W represents a C$_3$ or C$_4$ alkylene group or a group of formula —(CH$_2$)$_k$—S—(CH$_2$)$_l$—, wherein k represents the cypher 0 or the integer 1 and l represents an integer from 1 to 3;
m represents the integer 1 or 2; and
n represents the integer 2;
R[2] represents a phenyl group, a thienyl group, a furyl group, an oxazolyl group, an isoxazolyl group, a thiazolyl group or a 1,3,4-thiadiazolyl group;
B represents a methylene group; and
Y represents a sulfur atom or a methylene group;
or a pharmaceutically acceptable salt thereof.

40. A method as claimed in claim 37, wherein said antihypotensive agent is a compound of formula (I) in which:
A represents a group of formula H$_2$N—Z—, in which Z represents a C$_7$ or C$_8$ alkylene group;
R[2] represents a phenyl group, a 2-thienyl group, a 3-thienyl group or a 2-furyl group;
B represents a methylene group; and
Y represents a sulfur atom or a methylene group;
or a pharmaceutically acceptable salt thereof.

41. A method as claimed in claim 37, wherein said antihypotensive agent is a compound of formula (I) in which:
A represents a group of formula H$_2$N—Z—, in which Z represents a C$_7$ or C$_8$ alkylene group;
R[2] represents a 2-thienyl group, a 3-thienyl group or a 2-furyl group;
B represents a methylene group; and
Y represents a sulfur atom;
or a pharmaceutically acceptable salt thereof.

42. A method as claimed in claim 37, wherein said antihypotensive agent is a compound of formula (I) in which:
A represents a group of formula (iia):

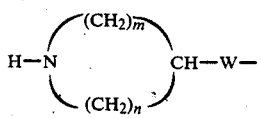

in which:
W represents a tetramethylene group or a group of formula —(CH$_2$)$_k$—S—(CH$_2$)$_l$—, wherein k represents the cypher 0 or the integer 1 and l represents an integer from 1 to 3;
m represents the integer 2; and
n represents the integer 2;
R[2] represents a phenyl group, a 2-thienyl group, a 3-thienyl group or a 2-furyl group;
B represents a methylene group; and
Y represents a sulfur atom or a methylene group;
or a pharmaceutically acceptable salt thereof.

43. A method as claimed in claim 37, wherein said antihypotensive agent is a compound of formula (I) in which:
A represents a group of formula (iia):

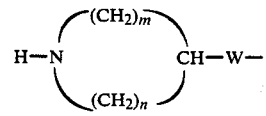

in which:
W represents a tetramethylene group or a group of formula —(CH$_2$)$_k$—S—(CH$_2$)$_l$—, wherein k represents the cypher 0 or the integer 1 and l represents an integer from 1 to 3;
m represents the integer 2; and
n represents the integer 2;
R[2] represents a 2-thienyl group, a 3-thienyl group or a 2-furyl group;
B represents a methylene group; and
Y represents a sulfur atom;
or a pharmaceutically acceptable salt thereof.

44. A method as claimed in claim 37, wherein said hypotensive agent is selected from the group consisting of:
α-[6-(8-amino-1-carboxyoctylamino)-5-oxo-2-(2-thienyl)perhydro-1,4-thiazepin-4-yl]acetic acid;
α-[6-(9-amino-1-carboxynonylamino)-5-oxo-2-(2-thienyl)perhydro-1,4-thiazepin-4-yl]acetic acid;
α-[6-(8-amino-1-carboxyoctylamino)-5-oxo-2-(3-thienyl)perhydro-1,4-thiazepin-4-yl]acetic acid;
α-[6-(8-amino-1-carboxyoctylamino)-5-oxo-2-(2-furyl)perhydro-1,4-thiazepin-4-yl]acetic acid;

α-[6-(8-amino-1-carboxyoctylamino)-5-oxo-2-phenyl-perhydro-1,4-thiazepin-4-yl]acetic acid;
α-[3-(8-amino-1-carboxyoctylamino)-2-oxo-6-(2-thienyl)perhydroazepin-1-yl]acetic acid;
α-[3-(9-amino-1-carboxynonylamino)-2-oxo-6-(2-thienyl)perhydroazepin-1-yl]acetic acid;
α-[3-(8-amino-1-carboxyoctylamino)-2-oxo-6-phenyl-perhydroazepin-1-yl]acetic acid;
α-[3-(9-amino-1-carboxynonylamino)-2-oxo-6-phenylperhydroazepin-1-yl]acetic acid;
α-(6-[1-carboxy-5-(4-piperidyl)pentylamino]-5-oxo-2-(2-thienyl)perhydro-1,4-thiazepin-4-yl)acetic acid;
α-(6-[1-carboxy-5-(4-piperidyl)pentylamino]-5-oxo-2-phenylperhydro-1,4-thiazepin-4-yl]acetic acid;
α-{6-[1-carboxy-5-(4-piperidyl)pentylamino]-5-oxo-2-(3-thienyl)perhydro-1,4-thiazepin-4-yl]acetic acid;
α-{6-[1-carboxy-5-(4-piperidyl)pentylamino]-5-oxo-2-(2-furyl)perhydro-1,4-thiazepin-4-yl]acetic acid;
α-{3-[1-carboxy-5-(4-piperidyl)pentylamino]-2-oxo-6-(2-thienyl)perhydroazepin-1-yl}acetic acid;
α{3-[1-carboxy-5-(4-piperidyl)pentylamino]-2-oxo-6-(3-thienyl)perhydroazepin-1-yl}acetic acid;
α-{3-[1-carboxy-5-(4-piperidyl)pentylamino]-2-oxo-6-phenylperhydroazepin-1-yl}acetic acid;
and pharmaceutically acceptable salts thereof.

* * * * *

UNITED STATES PATENT AND TRADEMARK OFFICE
CERTIFICATE OF CORRECTION

PATENT NO. : 4,778,790

DATED : October 18, 1988

INVENTOR(S) : YANAGISAWA et al

It is certified that error appears in the above-identified patent and that said Letters Patent is hereby corrected as shown below:

Column 5, line 48, change "$C_1-C_4$" to --$C_1-C_6$--.

Column 6, line 10, change "or" to --and--.

Column 14, line 40, change "α-o6(R)-..." to --α-(6(R)-...--.

Column 19, line 5, change "$[=]_D$." to --$[\alpha]_D$.--.

Column 27, line 65, change "pached" to --packed--.

Signed and Sealed this

Twenty-sixth Day of May, 1992

Attest:

DOUGLAS B. COMER

Attesting Officer     Acting Commissioner of Patents and Trademarks